United States Patent
Sato et al.

(10) Patent No.: US 7,838,692 B2
(45) Date of Patent: *Nov. 23, 2010

(54) ALKYL ACETAL COMPOUND, PROCESS FOR PRODUCING THE SAME, AND LUBRICATING OIL COMPOSITION

(75) Inventors: Haruhito Sato, Chiba (JP); Akihiro Shishikura, Chiba (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 10/590,603

(22) PCT Filed: Feb. 22, 2005

(86) PCT No.: PCT/JP2005/002802

§ 371 (c)(1),
(2), (4) Date: Aug. 24, 2006

(87) PCT Pub. No.: WO2005/080305

PCT Pub. Date: Sep. 1, 2005

(65) Prior Publication Data

US 2008/0234152 A1    Sep. 25, 2008

(30) Foreign Application Priority Data

Feb. 25, 2004 (JP) ............................. 2004-049093
Feb. 25, 2004 (JP) ............................. 2004-049180

(51) Int. Cl.
*C07D 317/12* (2006.01)
(52) U.S. Cl. ..................................... 549/369
(58) Field of Classification Search ........................ None
See application file for complete search history.

(56) References Cited

U.S. PATENT DOCUMENTS 4,631,292 A * 12/1986 Tomiyama et al. .......... 514/452

FOREIGN PATENT DOCUMENTS

| JP | 7-508547 | 9/1995 |
| JP | 8-208814 | 8/1996 |
| JP | 10-8080 | 1/1998 |
| JP | 10-245354 | 9/1998 |
| JP | 11-193390 | 7/1999 |
| JP | 11-209781 | 8/1999 |
| JP | 11-513742 | 11/1999 |
| JP | 11-349975 | 12/1999 |
| JP | 2000-96073 | 4/2000 |
| JP | 2000-186291 | 7/2000 |
| JP | 2000-186292 | 7/2000 |
| JP | 2000-263125 | 9/2000 |
| JP | 2001-031671 | 2/2001 |
| JP | 2002-327193 | 11/2002 |
| JP | 2003-238978 | 8/2003 |

OTHER PUBLICATIONS

Mazet, Neopentylic rearrangement of 2,2-disubstituted-1,3-propanediols in acid, Bulletin de la Societe Chimique de France, 1969, (12), pp. 4309-4321 and CAPLUS printout.*
Annex to Official Journal of the European Communities, Jun. 15, 1990, CHEMLIST printout.*
Cramarossa et al., Acetals by AlFe-Pillard Montomorillonate Catalysis, Tetrahedron, vol. 53, No. 46, pp. 15889-15894.*
Nerdel et al., Justus Liebigs Annalen Der Chemie, 1967, vol. 1967:710, pp. 85-89.*
Registry (STN) [ online ], Aug. 31, 1985, [ retrieval date May 9, 2005 ], CAS registration No. 93893-48-2.
Yarovaya, O. I. et al., "Acid-catalyzed Reactions of Camphene and α-Frenchene Epoxides", Russian Journal of Organic Chemistry, vol. 38, No. 6, pp. 810-822, 2002.
IUPAC Rule A-2 "Acyclic Hydrocarbons, " accessed Dec. 8, 2009.

* cited by examiner

*Primary Examiner*—Rosalynd Keys
(74) *Attorney, Agent, or Firm*—Oblon, Spivak, McClelland, Maier & Neustadt, L.L.P.

(57) ABSTRACT

A compound which satisfies requirements for the annealing property and the lubricating property simultaneously and a process for producing the compound are provided. The compound is an alkylacetal compound represented by the following general formula (1) or (2). In the general formulae, $R^1$ and $R^2$ represent hydrocarbon groups, $R^3$ to $R^8$ represent hydrogen atom or hydrocarbon groups, i and j represent integers satisfying the relation that the sum of the integers is 8 to 98, and k represents 0 or 1.

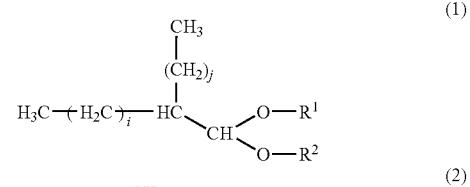

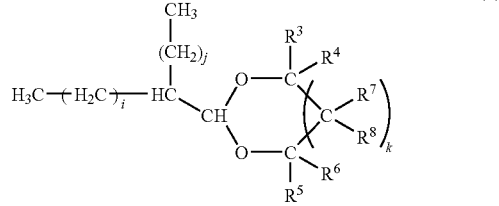

2 Claims, 16 Drawing Sheets

ALKYL ACETAL COMPOUND, PROCESS FOR PRODUCING THE SAME, AND LUBRICATING OIL COMPOSITION

TECHNICAL FIELD

The present invention relates to an alkylacetal compound advantageously used as a component of a lubricating oil composition, in particular, a drawing oil composition for producing copper tubes and a process for producing the compound.

The present invention also relates to a lubricating oil composition for metalworking which uses the above compound, exhibits an excellent lubricating property at high temperatures and is advantageously used for metalworking such as cold rolling, drawing, extruding, forging, pressing, bending, stretch-expand forming and squeezing and, more particularly, to a lubricating oil composition for metalworking which is advantageously used for working copper-based metals such as copper and copper alloy.

BACKGROUND ART

The lubricating property is required for oils such as cutting oil, grinding oil, polishing oil, rolling oil, drawing oil, pressing oil, forging oil and metalworking oils used for working silicon wafers such as polishing and cutting. As the metalworking oil, in general, oils insoluble in water which are prepared by adding various additives to mineral oils or oils soluble in water which are prepared by adding various additives to mineral oils or synthetic oils and used after being diluted with water, are used. Heretofore, the lubricating property of metalworking oils based on mineral oils such as emulsion-based cutting oils and non-aqueous cutting oils are improved by adding an oiliness improver such as a fatty acid ester and a fatty acid or an extreme pressure additive containing an element such as sulfur, chlorine and phosphorus. However, the use of the extreme pressure additive containing chlorine has become difficult due to destruction of the ozonosphere, and the use of the extreme pressure additive containing phosphorus has become difficult due to the environmental problems such as the eutrophication caused by factory disposal. Although an excellent lubricating property can be obtained by using a polyether, it is difficult that the appearance of the product is made uniform due to poor compatibility of the polyether with hydrocarbon-based base oils such as mineral oils.

Among various metals, copper has the characteristic that excellent thermal conductivity and excellent workability are exhibited. Among the applications of copper-based metals, copper piping used for heat exchangers of air conditioners is one of applications regulated by the most rigorous quality standards. In general, copper tubes used for this piping are produced by drawing and shipped after cleaning, drying and annealing. In the drawing, the condition of the working is severe and, in general, it is necessary that an excellent lubricant satisfying viscosity characteristic and workability be used.

As the oil composition for metalworking and the lubricating oil composition, the following compositions have been disclosed: metalworking oil compositions containing oxygen-bearing compounds which are selected from alkylene oxide adducts of polyhydric alcohols having 3 to 6 hydroxyl groups and hydrocarbyl ethers of alkylene oxide adducts of polyhydric alcohols having 3 to 6 hydroxyl groups or oxygen-bearing compounds which are selected from specific polyalkylene glycols, hydrocarbyl ethers of specific polyalkylene glycols and dihydric alcohols having 2 to 8 carbon atoms (for example, Japanese Patent Application Laid-Open No. Heisei 10 (1998)-8080); lubricating oil compositions containing a polyester composition for lubricant containing a polyester having a viscosity of 3,000 to 25,000 cps and obtained by reacting a partial ester with a dibasic acid in an amount of 0.7 to 1.0 moles per 1 mole of the partial ester, wherein the partial ester is obtained by reacting a polyol having a functionality of 3 to 6 with a fatty acid having 12 to 22 carbon atoms in a manner such that the residual hydroxy group of the polyol shows a functionality of 2.0 to 2.5, (for example, Japanese Patent Application Laid-Open No. Heisei 8 (1996)-208814); metalworking oil compositions containing an additive which contains a reaction product of an epoxidized alkyl ester of a fatty acid and an amine compound (for example, Japanese Patent Application Laid-Open No. 2000-186292); and metalworking oils comprising a specific polyether having an HLB of 6.0 or smaller and a weight-average molecular weight of 500 to 30,000 (for example, Japanese Patent Application Laid-Open No. 2003-238978). However, these lubricating oil compositions for metalworking do not satisfy the requirements for the annealing property and the lubricating property simultaneously.

On the other hand, copper has the characteristic that excellent thermal conductivity and excellent workability are exhibited. Among the applications of copper-based metals, copper piping used for heat exchangers of air conditioners is one of applications regulated by the most rigorous quality standards. In general, copper tubes used for this piping are produced by drawing and shipped after cleaning, drying and annealing. In the drawing, the condition of the working is severe and, in general, it is necessary that an excellent satisfying viscosity chracteristic and workability be used (for example, Japanese Patent Application Laid-Open No. 2000-263125).

However, recently, a process without cleaning with an organic solvent is desired from the standpoint of the environment. Based on the efforts by manufacturers of lubricants, drawing oils for producing copper tubes using an easily thermally decomposable macromolecular substance such as polybutene as the base oil have been developed to replace oils using mineral oils as the base oil (for example, Japanese Patent Application Laid-Open Nos. Heisei 11 (1999)-193390, Heisei 11 (1999)-209781, Heisei 11 (1999)-349975, 2000-96073 and 2000-186291).

However, since the cleaning step of the drawing oil is omitted in the process for producing copper tubes, a great problem arises in that the color of copper tubes changes when a conventionally used strong sulfur-based extreme pressure additive is used in the production of the copper tubes. Another great problem is the amount of residual oil. The standard for the residual oil in Japan is as severe as 0.1 mg/m. The oil mainly used at present is prepared by adding a fatty acid ester-based additive and has a viscosity characteristic. When this oil is used, side reactions take place due to heating during the annealing, and it is difficult that the amount of the residual oil is decreased.

DISCLOSURE OF THE INVENTION

The present invention has been made under the above circumstances and has an object of providing a compound which satisfies requirements for the annealing property and the lubricating property simultaneously and a process for producing the compound.

The present invention has a further object of providing a lubricating oil composition for metalworking which exhibits the excellent lubricating property (small friction) at high temperatures and is advantageously used for metalworking such as cold rolling, drawing, extruding, forging, pressing, bending, stretch-expand forming and squeezing and, more particularly, to a lubricating oil composition for metalworking which is advantageously used for working copper-based metals such as copper and copper alloy.

As the result of extensive studies by the present inventors to overcome the above problems, it was found that alkylacetal compounds in which the alkyl group had a linear alkyl group at the 2-position as a branch satisfied the annealing property and the lubricating property simultaneously and provided properties more excellent than those provided with, for example, benzotriazole derivatives.

As the result of extensive studies by the present inventors to overcome the above problems, it was also found that a lubricating oil composition comprising a base oil and a specific compound had the lubricating property and the workability which are the same as or more excellent than those of conventional fatty acid esters, could be used in a wider temperature range than conventional fatty acid esters and alcohols could and did not remain after the annealing. The present invention has been completed based on the above knowledge.

The present invention provides the following alkylacetal compounds and the processes for producing the compounds. The present invention also provides the following lubricating oil compositions for metalworking.

1. An alkylacetal compound having a structure represented by following general formula (1):

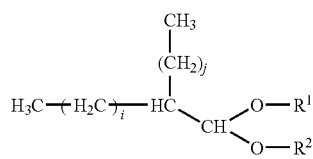

(1)

wherein $R^1$ and $R^2$ each independently represent a hydrocarbon group, and i and j each represent an integer satisfying a relation that a sum of the integers is in a range of 8 to 98.

2. An alkylacetal compound described in 1., wherein i represents n, and j represents n+2, n representing an integer in a range of 3 to 48.

3. An alkylacetal compound having a structure represented by following general formula (2):

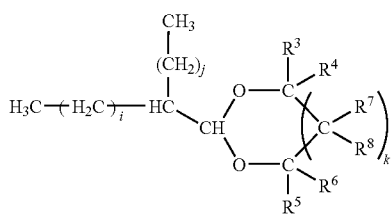

(2)

wherein $R^3$ to $R^8$ each independently represent hydrogen atom or a hydrocarbon group, k represents 0 or 1, and i and j each represent an integer satisfying a relation that a sum of the integers is in a range of 8 to 98.

4. An alkylacetal compound described in 3., wherein i represents n, and j represents n+2, n representing an integer in a range of 3 to 48.

5. An alkylacetal compound described in 4., which is represented by following general formula (3):

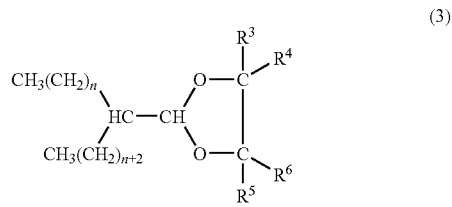

(3)

wherein $R^3$ to $R^6$ are as defined in general formula (2), and n represents an integer in a range of 3 to 48.

6. A process for producing an alkylacetal compound described in any one of 1. and 5. which comprises reacting an alcohol with an epoxide represented by following general formula (4):

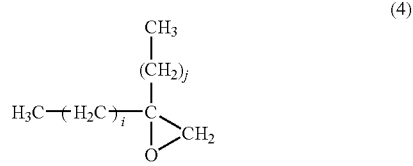

(4)

wherein i and j each represent an integer satisfying a relation that a sum of the integers is in a range of 8 to 98.

7. A process for producing an alkylacetal compound described in 6., wherein the epoxide is a compound represented by following general formula (5):

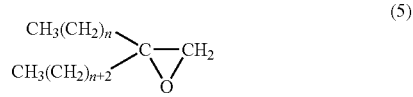

(5)

wherein n represents an integer in a range of 3 to 48.

8. A process for producing an alkylacetal compound described in any one of 1. and 5. which comprises reacting an alcohol with an aldehyde represented by following general formula (6):

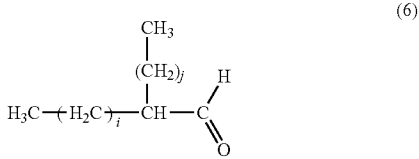

(6)

wherein i and j each represent an integer satisfying a relation that a sum of the integers is in a range of 8 to 98.

9. A process for producing an alkylacetal compound described in 8., wherein the aldehyde is a compound represented by following general formula (7):

$$CH_3(CH_2)_n \diagdown CH_3(CH_2)_{n+2} \diagup CH-C \diagdown_O^H \quad (7)$$

wherein n represents an integer in a range of 3 to 48.

10. A process for producing an alkylacetal compound described in any one of 6. to 9., wherein the alkylacetal compound represented by general formula (2) is produced using as the alcohol a glycol represented by following general formula (8):

$$HO-C(R^3)(R^4)-(C(R^7)(R^8))_k-C(R^5)(R^6)-OH \quad (8)$$

wherein $R^3$ to $R^8$ reach independently represent hydrogen atom or a hydrocarbon group, and k represents 0 or 1.

11. A process described in 10., wherein the glycol is a compound selected from ethylene glycol, propylene glycol, 1,3-trimethylene glycol, derivatives of 1,3-trimethylene glycol and 1,2-butanediol.

12. A lubricating oil composition for metalworking which comprises a base oil and at least 1% by mass based on a mass of the composition of at least one compound selected from dioxolane compounds represented by following general formula (11), dioxolane compounds represented by following general formula (12), dioxane compounds represented by following general formula (13) and dioxane compounds represented by following general formula (14):

(11) 1,3-dioxolane with substituents $R^{11}, R^{12}$ on C2 and $R^{13}, R^{14}, R^{15}, R^{16}$ on C4, C5.

(12) 1,3-dioxolane with substituents $R^{17}, R^{18}$ and $R^{19}, R^{20}, R^{21}, R^{22}$.

(13) 1,3-dioxane with substituents $R^{23}, R^{24}, R^{25}, R^{26}, R^{27}, R^{28}, R^{29}, R^{30}$.

(14) 1,4-dioxane with substituents $R^{31}$ through $R^{38}$.

wherein $R^{11}$ to $R^{38}$ each independently represent hydrogen atom or a group selected from saturated hydrocarbon groups having 1 to 30 carbon atoms, unsaturated hydrocarbon groups having 1 to 30 carbon atoms and hydrocarbon groups having 1 to 30 carbon atoms and having ether bond, ester bond or hydroxyl group.

13. A lubricating oil composition for metalworking described in 12., wherein at least one of $R^{11}$ to $R^{38}$ in general formulae (11) to (14) represents a hydrocarbon group having a hydrocarbon chain having nitrogen atom.

14. A lubricating oil composition for metalworking described in any one of 12. and 13., wherein the base oil is at least one compound selected from polybutene, polyisobutylene and polyalkylene glycols insoluble in water and has a kinematic viscosity in a range of 5 to 3,000 mm$^2$/s at 40° C., and a content of the base oil is 95% by mass or smaller based on a mass of the composition.

15. A lubricating oil composition for metalworking described in any one of 12. to 14., which comprises at least 0.01% by mass based on a mass of the composition of at least one 2,2-dialkylepoxide compound represented by following general formula (15):

$$R^{39}-C(R^{40})\diagdown_O \quad (15)$$

wherein $R^{39}$ and $R^{40}$ each independently represent a group selected from saturated hydrocarbon groups having 1 to 30 carbon atoms, unsaturated hydrocarbon groups having 1 to 30 carbon atoms and hydrocarbon groups having 1 to 30 carbon atoms and having ether bond, ester bond or hydroxyl group.

16. A lubricating oil composition for metalworking described in any one of 12. to 15., which comprises 0.01 to 10% by mass based on a mass of the composition of at least one of benzotriazole and derivatives thereof.

17. A lubricating oil composition for metalworking described in any one of 12. to 16., which is used for copper or a metal containing copper.

EFFECT OF THE INVENTION

A lubricating oil composition which satisfies requirements for the annealing property and the lubricating property simultaneously and can be advantageously used as the drawing oil composition for producing copper tubes can be obtained by adding the alkylacetal compound of the present invention to a base oil.

In accordance with the present invention, the lubricating oil composition for metalworking which exhibits an excellent lubricating property (small friction) at high temperatures and is advantageously used for metalworking such as cold rolling, drawing, extruding, forging, pressing, bending, stretch-expand forming and squeezing and, in particular, for working copper-based metals such as copper and copper alloy, is provided.

THE MOST PREFERRED EMBODIMENT TO CARRY OUT THE INVENTION

Figure 1:
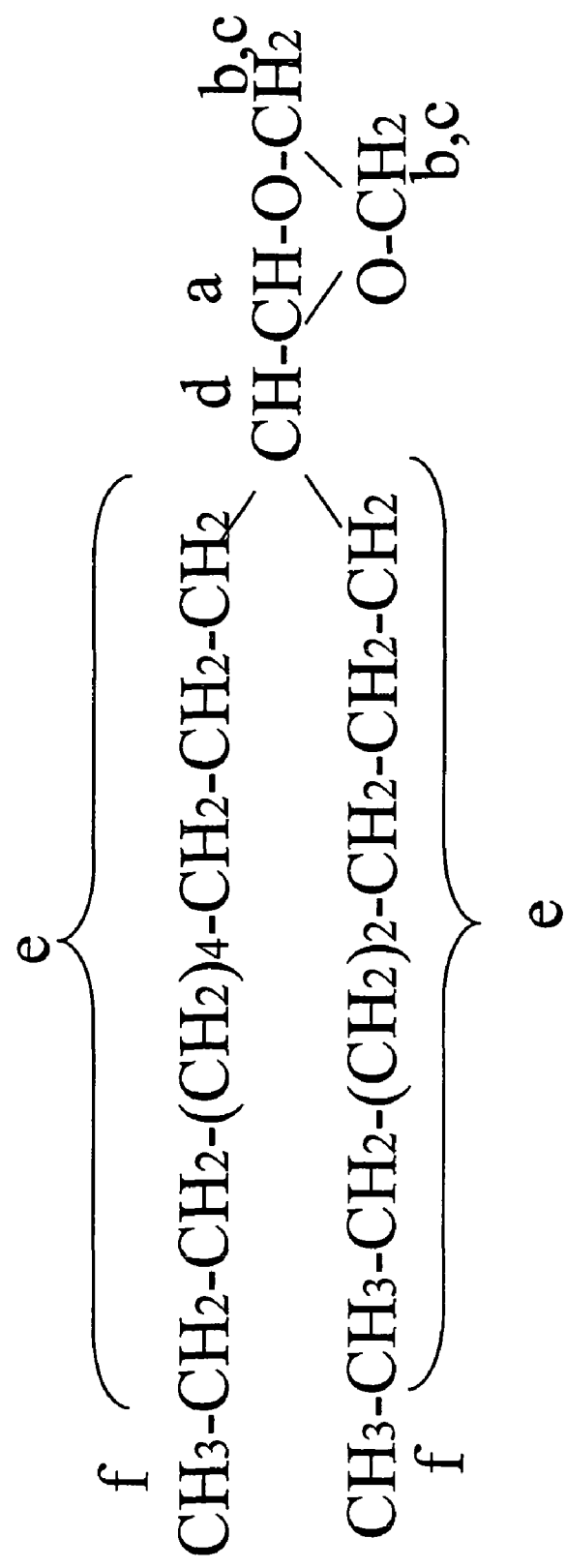
FIG. 1 shows a diagram exhibiting the marks assigned to hydrogen atoms in a 1,3-dioxolane compound in the $^1$H-NMR analysis.

The alkylacetal compounds of the present invention are novel compounds which are not described in any references and have the structures represented by the following general formulae (1) and (2):

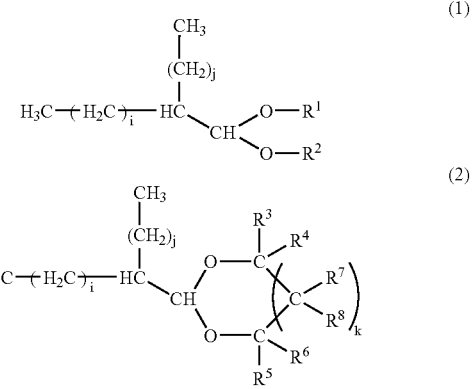

In the above general formula (1), $R^1$ and $R^2$ each independently represent a hydrocarbon group, and i and j each represent integers satisfying the relation that the sum of the integers is in the range of 8 to 98. In the above general formula (2), $R^3$ to $R^8$ each independently represent hydrogen atom or a hydrocarbon group, k represents 0 or 1, and and j are as defined above.

Examples of the hydrocarbon group described above include hydrocarbon groups having 1 to 20 carbon atoms in the entire molecule which may have suitable substituents and heteroatoms. It is preferable that the sum of the integers represented by i and j is in the range of 10 to 70 and more preferably in the range of 16 to 32.

As described above, the alkylacetal compound of the present invention has the structure in which a linear alkyl group has a linear alkyl group at the 2-position as a branch.

In the present invention, it is preferable from the standpoint of easiness of production that, in the general formulae (1) and (2) representing the alkylacetal compounds of the present invention, i represents n, and j represents n+2, wherein n represents an integer in the range of 3 to 48. It is more preferable that n represents an integer in the range of 3 to 33 and most preferably in the range of 7 to 15.

As for the alkyl(cyclic)acetal compound represented by the above general formula (2), it is preferable that k represents 0, i represents n, and j represents n+2, i.e., it is preferable that the alkyl(cyclic)acetal compound is a compound represented by the following general formula (3):

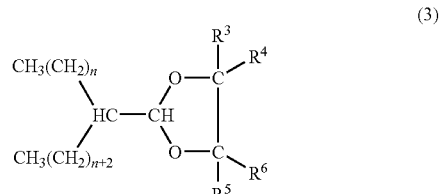

wherein $R^3$ to $R^6$ are as defined above, and n represents an integer in the range of 3 to 48.

The atom and the groups represented by $R^3$ to $R^8$ in the above general formula (2) and $R^3$ to $R^6$ in the above general formula (3) are decided by the type of the glycol used for producing the alkyl(cyclic acetal) compound. It is preferable that n described above represents an integer in the range of 3 to 33.

The process for producing the alkylacetal compounds represented by general formulae (1) and (2) is not particularly limited. The above alkylacetal compounds can be effectively produced in accordance with the process of the present invention which will be described in the following.

As for the process for producing the alkylacetal compound of the present invention, two embodiments thereof can be shown. The first embodiment will be described in the following. In the first embodiment of the process of the present invention, the alkylacetal compound represented by the above general formula (1) or (2) is produced by reacting an alcohol with an epoxide represented by the following general formula (4):

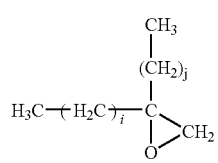
(4)

wherein i and j are as defined above. As the epoxide represented by the above general formula (4), compounds represented by the following general formula (5):

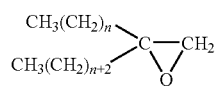
(5)

wherein n is as defined above, are preferable.

In the second embodiment, the alkylacetal compound represented by the above general formula (1) or (2) is produced by reacting an alcohol with an aldehyde represented by the following general formula (6):

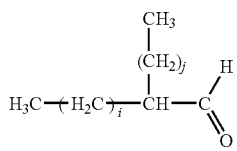
(6)

wherein i and j are as defined above. As the aldehyde represented by the above general formula (6), compounds represented by the following general formula (7):

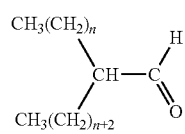
(7)

wherein n is as defined above, are preferable.

In the first embodiment and the second embodiment, the alkylacetal compound represented by general formula (1) can be obtained by using a monohydric alcohol as the alcohol. The alkyl(cyclic)acetal compound represented by the above general formula (2) can be obtained by using a glycol represented by the following general formula (8):

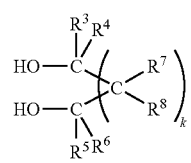
(8)

wherein $R^3$ to $R^8$ and k are as defined above.

As the glycol, for example, ethylene glycol, propylene glycol, 1,3-trimethylene glycol, derivatives of 1,3-trimethylene glycol and 1,2-butanediol are preferable, and α,β-alkanediols are more preferable. When a compound represented by the following general formula (9):

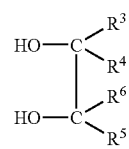
(9)

wherein $R^3$ to $R^6$ are as defined above, is used as the α,β-alkanediol, an alkyl(cyclic acetal) compound represented by the following general formula (10):

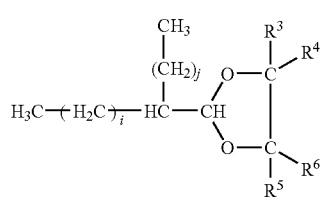
(10)

wherein $R^3$ to $R^6$, i and j are as defined above, is obtained. When i represents n, and j represents n+2, wherein n represents an integer in the range of 3 to 48, in the above general formula (10), the compound represented by general formula (10) is the alkyl(cyclic)acetal compound represented by the above general formula (3).

As the α,β-alkanediol represented by the above general formula (9), ethylene glycol, propylene glycol and 1,2-butanediol are preferable.

In the case of the first embodiment described above, the temperature of the reaction between the epoxide represented by the above general formula (4) and the alcohol is, in general, in the range of about 0 to 200° C. and preferably in the range of 20 to 140° C. The time of the reaction is, in general, in the range of about 1 to 48 hours and preferably in the range of 4 to 5 hours.

In the case of the second embodiment described above, Guerbet aldehyde synthesized by oxidation of Guerbet alcohol with an oxidizing agent such as chromium oxide and aldehydes synthesized from the above epoxides are preferable.

For example, when Guerbet aldehyde is used as the aldehyde and ethylene glycol is used as the alcohol, Guerbet aldehyde is slowly added dropwise to ethylene glycol containing a small amount of sulfuric acid under stirring and heating at a temperature, in general, in the range of about 50 to 200° C. and preferably in the range of 50 to 140° C. When the addition is completed, the stirring is continued, in general, for about 1 to 48 hours and preferably for 4 to 5 hours, and then the reaction is stopped. After the liquid-liquid separation of the reaction product, the alkyl(cyclic acetal) compound can be obtained from the upper layer.

When the alkylacetal compound of the present invention is mixed with a base oil, the composition which satisfies the requirements for the annealing property and the lubricating property simultaneously and can be advantageously used as the metalworking oil such as drawing oil compositions for producing copper tubes can be provided. In this case, 2-(long chain branched alkyl)-1,3-dioxolanes are preferable among the alkylacetal compounds of the present invention. As the base oil, mineral oils and/or synthetic oils can be used. The mineral oil and the synthetic oil are not particularly limited as long as the mineral oil and the synthetic oil can be used as the base oil of a lubricant. From the standpoint of the properties as the metalworking oil, it is preferable that the kinematic viscosity of the oil is in the range of 5 to 3,000 mm²/s and more preferably in the range of 10 to 3,000 mm²/s at 40° C. The pour point as the index for the fluidity of the base oil at low temperatures is not particularly limited. It is preferable that the pour point is −10° C. or lower.

As the mineral oil and the synthetic oil described above, various types of mineral oils and synthetic oils are available, and a suitable oil can be selected in accordance with the application. Examples of the mineral oil include paraffinic group-based mineral oils, naphthenic mineral oils and intermediate group-based mineral oils. Specific examples of the mineral oil include light neutral oil, intermediate neutral oil, heavy neutral oil and bright stock obtained by purification with solvent or purification by hydrogenation.

Examples of the synthetic oil include poly-α-olefins, α-olefin copolymers, polybutene, polyisobutylene, polyalkylene glycols insoluble in water, alkylbenzenes, polyol esters, esters of dibasic acids, polyoxyalkylene glycols, polyoxyalkylene glycol esters, polyoxyalkylene glycol ethers, hindered esters and silicone oils. The base oil can be used singly or in combination of two or more. A combination of a mineral oil and a synthetic oil may be used as the base oil.

In the present invention, easily thermally decomposable polymers, such as polybutene, polyisobutylene and polyalkylene glycols insoluble in water, having a kinematic viscosity at 40° C. in the range of 10 to 3,000 mm²/s are preferable. The lubricating oil composition obtained by adding the alkylacetal compound of the present invention to the easily thermally decomposable polymer satisfies the requirements for the annealing property (the easily decomposable property, the small amount of residual oil and no change in the color) and the lubricating property (small friction) in the metalworking to a greater degree. In particular, the composition interacts specifically with copper-based metals to form an adsorption film in an amount which is the same as or greater than that formed by adding a fatty acid ester-based additive, and the small friction coefficient can be maintained at high temperatures. In the working in which the lubricating property alone is mainly required and the requirement for the annealing property is limited, the above mineral oil can be used.

The above descriptions on the base oil can also be applied to the base oil in the lubricating oil composition for metalworking which will be described below.

In the lubricating oil composition, the amount of the alkylacetal compound of the present invention is, in general, 1% by mass or greater based on the amount of the composition. The amount can be suitably selected in accordance with the process and the condition of the working. For example, in the case of cold rolling of pure copper metal, an amount in the range of about 1 to 15% by mass is suitable. In the case of production of copper tubes by drawing, an amount in the range of about 5 to 30% by mass is preferable.

In general, the lubricating oil composition of the present invention may suitably comprise conventional additives such as stabilizers, oiliness improvers, extreme pressure additives, dispersants, corrosion inhibitors, antioxidants and defoaming agents to maintain the basic properties as the lubricant as long as the effect of the present invention is not adversely affected. The total amount of these additives is, in general, in the range of 0.01 to 20% by mass based on the amount of the composition.

The above descriptions on the additives can also be applied to the additives in the lubricating oil composition for metalworking which will be described in the following.

The lubricating oil composition for metalworking of the present invention comprises the base oil described above and 1% by mass based on the amount of the composition of at least one compound selected from dioxolane compounds represented by following general formula (11), dioxolane compounds represented by following general formula (12), dioxane compounds represented by following general formula (13) and dioxane compounds represented by following general formula (14):

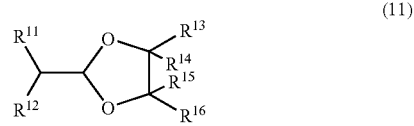

(11)

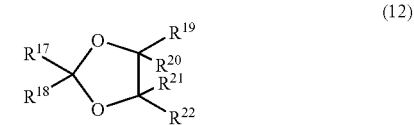

(12)

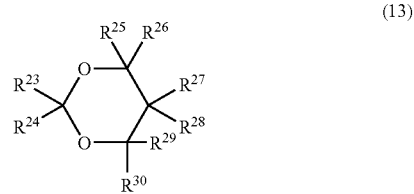

(13)

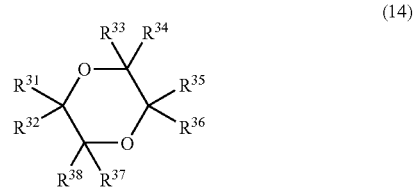

(14)

In the above formulae, $R^{11}$ to $R^{38}$ each independently represent hydrogen atom or a group selected from saturated hydrocarbon groups having 1 to 30 carbon atoms and preferably having 4 to 28 carbon atoms, unsaturated hydrocarbon groups having 1 to 30 carbon atoms and preferably having 4 to 28 carbon atoms and hydrocarbon groups having 1 to 30 carbon atoms, preferably having 4 to 28 carbon atom, and having ether bond, ester bond or hydroxyl group. At least one of the groups represented by $R^{11}$ to $R^{38}$ may be a hydrocarbon group having a hydrocarbon chain having nitrogen atom. Examples of the saturated hydrocarbon group having 1 to 30 carbon atoms include alkyl groups such as methyl group, ethyl group, n-propyl group, isopropyl group, n-butyl group, isobutyl group, sec-butyl group, tert-butyl group, various types of pentyl groups, various types of hexyl groups, various types of heptyl groups, various types of octyl groups, various types of nonyl groups, various types of decyl groups, various types of undecyl groups, various types of dodecyl groups, tridecyl groups, tetradecyl groups, pentadecyl groups, hexadecyl groups, heptadecyl groups, octadecyl groups, nonadecyl groups and eicosyl groups. Examples of the unsaturated hydrocarbon group having 1 to 30 carbon atoms include alkenyl groups such as vinyl group, propenyl group, allyl group, cyclohexenyl group and oleyl group.

Examples of the dioxolane compound represented by the above general formula (11) include 2-alkyl-1,3-dioxolanes having an alkyl group having 1 to 30 carbon atoms such as 2-hexyl-1,3-dioxolane, 2-heptyl-1,3-dioxolane, 2-octyl-1,3-dioxolane and 2-eicosyl-1,3-dioxolane; dioxolane compounds having a branched alkyl group as the side chain such as 2-(1-butylheptyl)-1,3-dioxolane, 2-(1-hexylnonyl)-1,3-dioxolane, 2-(1-octyldecyl)-1,3-dioxolane, 2-(1-octylundecyl)-1,3-dioxolane, 2-(1-decyl-tetradecyl)-1,3-dioxolane and 2-(1-octadecyleicosyl)-1,3-dioxolane; and 2-alkenyl-1,3-dioxolanes having a linear alkenyl group having 1 to 30 carbon atoms or a branched alkenyl group such as 2-(1-octenylundecyl)-1,3-dioxolane. Examples of the compound having a hydrocarbon group having 1 to 30 carbon atoms and having ether bond, ester bond or hydroxyl group include 2-alkyl-4-alkanol-1,3-dioxolanes such as 2-(1-octyldodecyl)-α,β-glycerol formal. In the present invention, dioxolane compounds having a branched alkyl group as the side chain are preferable.

Examples of the dioxolane compound represented by general formula (12) include 2,2'-dialkyl-1,3-dioxolanes such as 2-hexyl-2'-methyl-1,3-dioxolane, 2-heptyl-2'-methyl-1,3-dioxolane, 2-octyl-2'-methyl-1,3-dioxolane, 2-eicosyl-2'-methyl-1,3-dioxolane, 2-hexyl-2'-ethyl-1,3-dioxolane, 2-heptyl-2'-ethyl-1,3-dioxolane, 2-octyl-2'-ethyl-1,3-dioxolane, 2-eicosyl-2'-ethyl-1,3-dioxolane, 2-hexyl-2'-n-propyl-1,3-dioxolane, 2-heptyl-2'-n-propyl-1,3-dioxolane, 2-octyl-2'-n-propyl-1,3-dioxolane, 2-eicosyl-2'-n-propyl-1,3-dioxolane, 2-hexyl-2'-n-butyl-1,3-dioxolane, 2-heptyl-2'-n-butyl-1,3-dioxolane, 2-octyl-2'-n-butyl-1,3-dioxolane and 2-eicosyl-2'-n-butyl-1,3-dioxolane.

Examples of the dioxane compound represented by the above general formula (13) include 2-alkyl-1,3-dioxanes and 2-alkenyl-1,3-dioxanes having a linear hydrocarbon group having 1 to 30 carbon atoms, 2-alkyl-1,3-dioxanes and 2-alkenyl-1,3-dioxanes having a branched hydrocarbon group having 1 to 30 carbon atoms and 1,3-dioxane compounds having an alkyl group bonded at the 2-position and a hydrocarbon group which has 1 to 30 carbon atoms, has ether bond, ester bond or hydroxyl group and is bonded at the 4-position and/or the 6-position.

Examples of the dioxane compound represented by the above general formula (14) include 2-alkyl-1,4-dioxanes and 2-alkenyl-1,4-dioxanes having a linear hydrocarbon group having 1 to 30 carbon atoms, 2-alkyl-1,4-dioxanes and 2-alkenyl-1,4-dioxanes having a branched hydrocarbon group having 1 to 30 carbon atoms and 1,4-dioxane compounds having an alkyl group bonded at the 2-position and a hydrocarbon group which has 1 to 30 carbon atoms, has ether bond, ester bond or hydroxyl group and is bonded at the 5-position and/or the 6-position.

The amount of the above compounds in the lubricating oil composition is 1% by mass or greater based on the amount of the composition. The amount can be suitably adjusted in accordance with the process and the condition of working. For example, in the case of cold rolling of pure copper metal, it is suitable that the amount is in the range of about 1 to 15% by mass. In the case of the production of copper tubes by drawing, it is preferable that the amount is in the range of about 5 to 30% by mass.

It is preferable that the lubricating oil composition of the present invention comprises at least one of the 2,2-dialkylepoxide compounds represented by the following general formula (15):

wherein $R^{39}$ and $R^{40}$ each independently represent a group selected from a saturated hydrocarbon group having 1 to 30 carbon atoms, an unsaturated hydrocarbon group having 1 to 30 carbon atoms and a hydrocarbon group having 1 to 30 carbon atoms and having ether bond, ester bond or hydroxyl group, in an amount of 0.01% by mass or greater based on the amount of the composition to prevent hydrolysis of the acetal bond due to a small amount of chlorine ion present in the base oil or a small amount of water mixed into the composition during working. The maximum amount of the above compound is, in general, about 5% by mass.

Examples of the compound represented by the above general formula (15) include 2-octyl-1,2-epoxydodecane.

The lubricating oil composition of the present invention may comprise benzotriazole and/or derivatives thereof which are known as the stabilizer for copper-based metals in an amount of 0.01 to 10% by mass based on the amount of the composition. It is preferable that the amount is in the range of 0.05 to 5% by mass. The effect of adding the above compound can be exhibited when the amount is 0.01% or greater. The above compound can be easily dissolved when the amount is 10% or smaller. Benzotriazole is the compound expressed by the following formula (16):

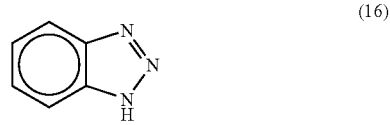

Examples of the derivative of benzotriazole include compounds represented by the following general formulae (17) to (19):

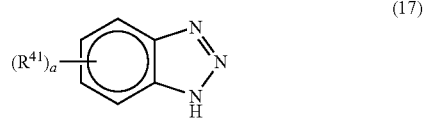

In general formula (17), $R^{41}$ represents an alkyl group having 1 to 4 carbon atoms, and a represents a number in the range of 1 to 3.

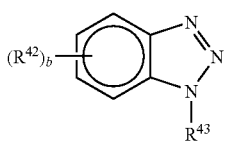

(18)

In general formula (18), $R^{42}$ and $R^{43}$ each independently represent an alkyl group having 1 to 4 carbon atoms, and b represents a number in the range of 0 to 3.

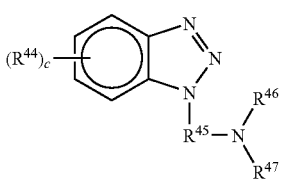

(19)

In general formula (19), $R^{44}$ represents an alkyl group having 1 to 4 carbon atoms, $R^{45}$ represents methylene group or ethylene group, $R^{46}$ and $R^{47}$ each independently represent hydrogen atom or a group selected from alkyl groups having 1 to 12 carbon atoms, and c represents a number in the range of 0 to 3.

EXAMPLES

The present invention will be described more specifically with reference to examples in the following. However, the present invention is not limited to the examples.

Example 1

Synthesis of a 2-(long chain branched alkyl)-1,3-dioxolane which is an alkyl(cyclic acetal) compound (1) Synthesis of 2-octyl-1-dodecene Into a three-necked flask having an inner volume of 5 liters and purged with nitrogen, 3.0 kg of 1-decene, 0.9 g (3 mmole) of zirconocene dichloride which is a metallocene complex and methylalumoxane (manufactured by ALBEMARLE Corporation; 8 mmole expressed as the amount of aluminum) were successively placed, and the resultant mixture was stirred at the room temperature (about 20° C.). The color of the reaction fluid changed from yellow to reddish brown. When 48 hours had passed after the start of the reaction, the reaction was stopped by adding methanol. Then, an aqueous solution of hydrochloric acid having a concentration of 2% by mass was added to the reaction fluid, and the formed organic layer was washed. The organic layer was treated by vacuum distillation, and 2.5 kg of a fraction having a boiling point range of 120 to 125° C./26.7 Pa (0.2 Torr) (a dimer of decene) was obtained. This fraction was analyzed in accordance with the gas chromatography, and it was found that the concentration of the dimer was 99% by mass, and the fraction of the vinylideneolefin in the dimer was 97% by mass.

(2) Synthesis of 2-octyl-1,2-epoxydodecane

Into a three-necked flask having an inner volume of 2 liters, 300 g of the dimer of decene synthesized above in (1) and 500 ml of toluene were placed and mixed together. The temperature of the mixture was kept at 70° C., and 150 g of an aqueous solution of hydrogen peroxide having a concentration of 30% by mass, 0.5 g of concentrated sulfuric acid and 20 g of formic acid were added. After the resultant mixture was stirred at the same temperature for 1.5 hours, the reaction product was poured into 500 ml of water, and the formed organic layer was washed with water. The organic layer was transferred to a flask, and 150 g of an aqueous solution of hydrogen peroxide having a concentration of 30% by mass, 0.5 g of concentrated sulfuric acid and 20 g of formic acid were added. After the obtained mixture was stirred at the temperature of 70° C. for 1.5 hours, the resultant mixture was treated by the liquid-liquid separation. The organic layer was separated, washed with water and dried. Toluene used as the solvent was removed under a reduced pressure, and 302 g of a concentrated fluid was obtained. The concentrated fluid was analyzed in accordance with $^1$H-NMR, and it was found that the content of 2-octyl-1,2-epoxydodecane was 94%.

(3) Synthesis of a 2-(long chain branched alkyl)-1,3-dioxolane compound

Into a three-necked flask having an inner volume of 500 ml and equipped with a dropping funnel and a reflux condenser, 200 ml of ethylene glycol (manufactured by WAKO JUN-YAKU Co., Ltd; Special Reagent Grade) and 2 g of concentrated sulfuric acid (the concentration: 96% by mass or greater) were placed, and the content was heated at 80° C. While the content was stirred at this temperature, 42.5 g (0.143 moles) of 2-octyl-1,2-epoxydodecane synthesized above in (2) was slowly added dropwise over 8 hours. After the addition was completed, the resultant mixture was stirred for 1 hour, and then the temperature was lowered. The reaction product was treated by the liquid-liquid separation. The upper layer was washed with water and dried, and 57.4 g (the yield: 79.3% by mole) of 2-(1-octylundecyl)-1,3-dioxolane (a 2-(long chain branched alkyl (the number of carbon atoms: 19))-1,3-dioxolane compound which was an alkyl(cyclic)acetal compound) having a purity of 71% by mass was obtained.

(4) Analysis of the structure of the 2-(long chain branched alkyl)-1,3-dioxolane compound The 2-(long chain branched alkyl)-1,3-dioxolane compound synthesized above in (3) in an amount of 10.0 g was dissolved in hexane, and the obtained solution was developed in a column packed with 200 g of silica gel (the moving phase: hexane). After the development was conducted with 2 liters of hexane, the development was further conducted with 1 liter of a mixed solvent containing hexane and diethyl ether in relative amounts by volume of 95:5. The elution of the 2-(long chain branched alkyl)-1,3-dioxolane compound took place during the development with the mixed solvent. The substance obtained by the elution was concentrated, and 7.4 g of the dioxolane compound having a purity of 85% by mass was isolated.

The 2-(long chain branched alkyl)-1,3-dioxolane compound having the increased purity obtained as described above was analyzed in accordance with $^1$H-NMR, $^{13}$C-NMR and two-dimensional NMR analyses (2D-COSY: Correlation Spectroscopy; 2D-HMQC: Hetero Nuclear Multi Quantum Coherence; and 2D-INADEQUATE: Incredible Natural Abundance Double Quantum Transfer Experiment), and the structure of the 1,3-dioxolane compound was elucidated.

FIG. 1 shows a diagram exhibiting the marks assigned to hydrogen atoms in the 1,3-dioxolane compound in the $^1$H-NMR analysis.

Figure 2:
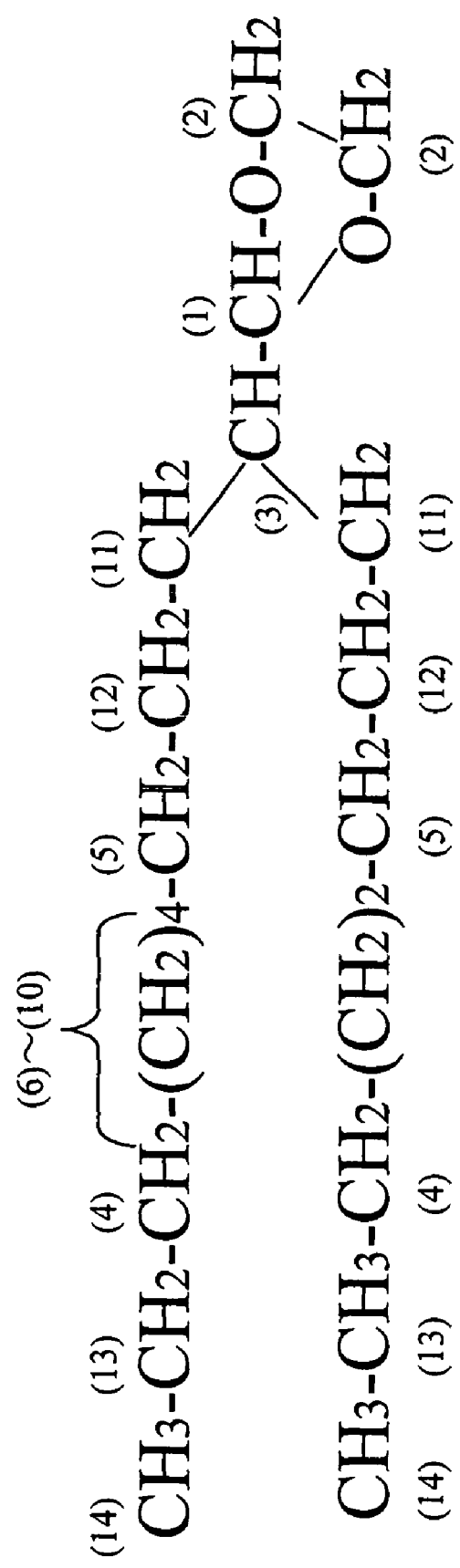
FIG. 2 shows a diagram exhibiting the marks assigned to carbon atoms in a 1,3-dioxolane compound in the $^{13}$C-NMR analysis.

FIG. 2 shows a diagram exhibiting the marks assigned to carbon atoms in the 1,3-dioxolane compound in the $^{13}$C-NMR analysis.

Figure 3:
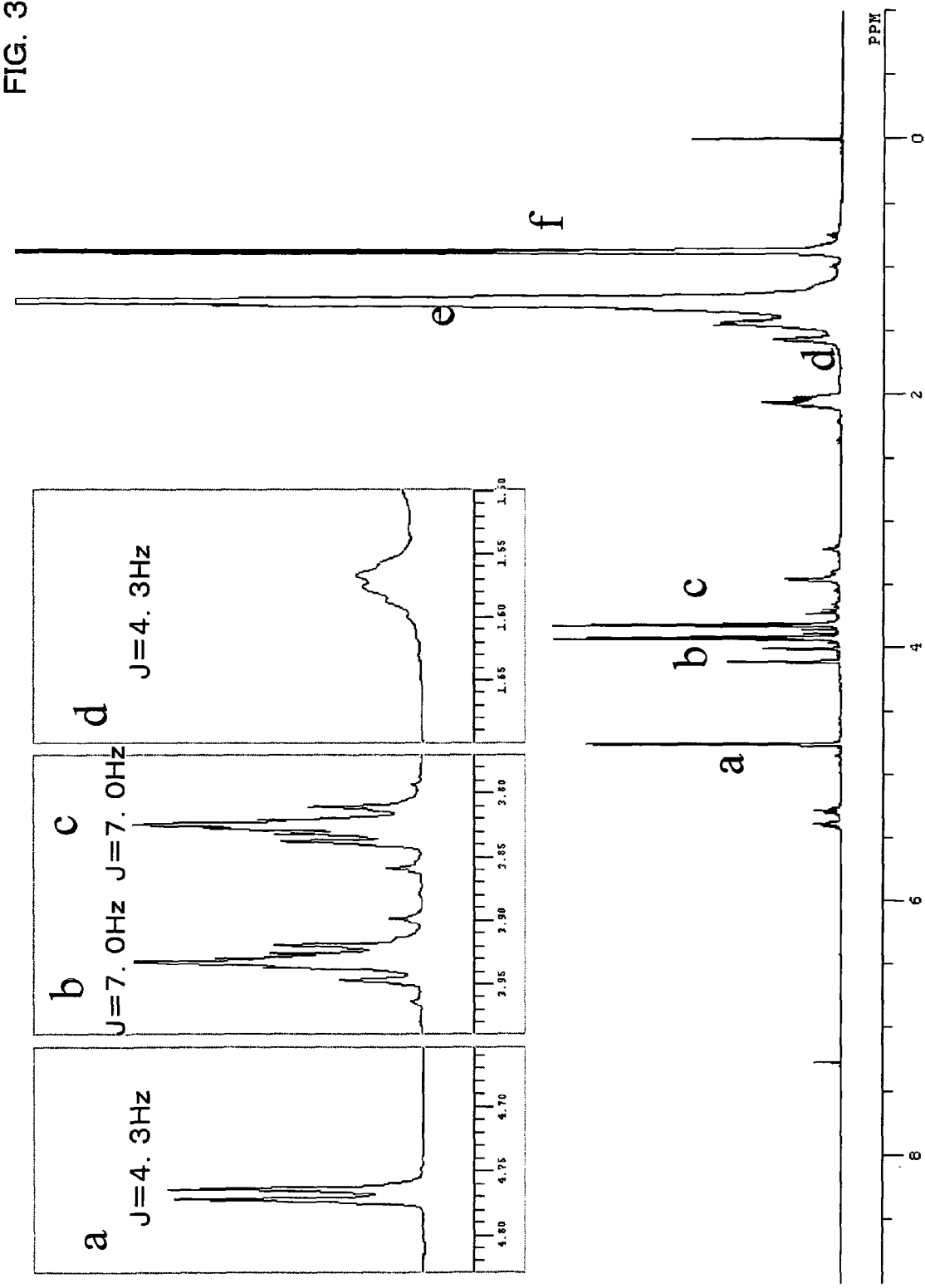
FIG. 3 shows a diagram exhibiting the data profile of $^1$H-NMR in the detailed analysis of a 1,3-dioxolane compound.
Figure 4:
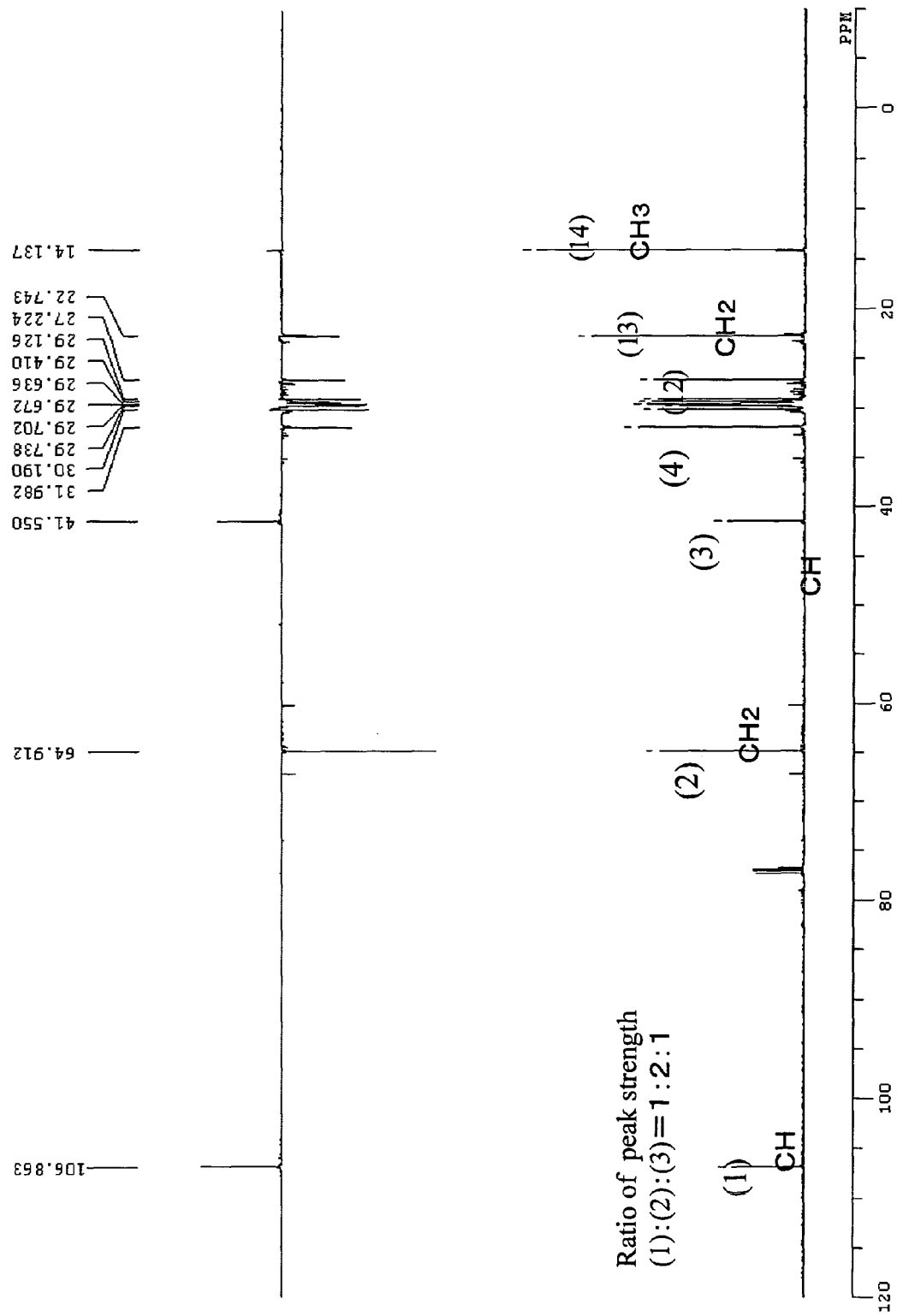
FIG. 4 shows a diagram exhibiting the data profile of $^{13}$C-NMR in the detailed analysis of a 1,3-dioxolane compound.
Figure 5:
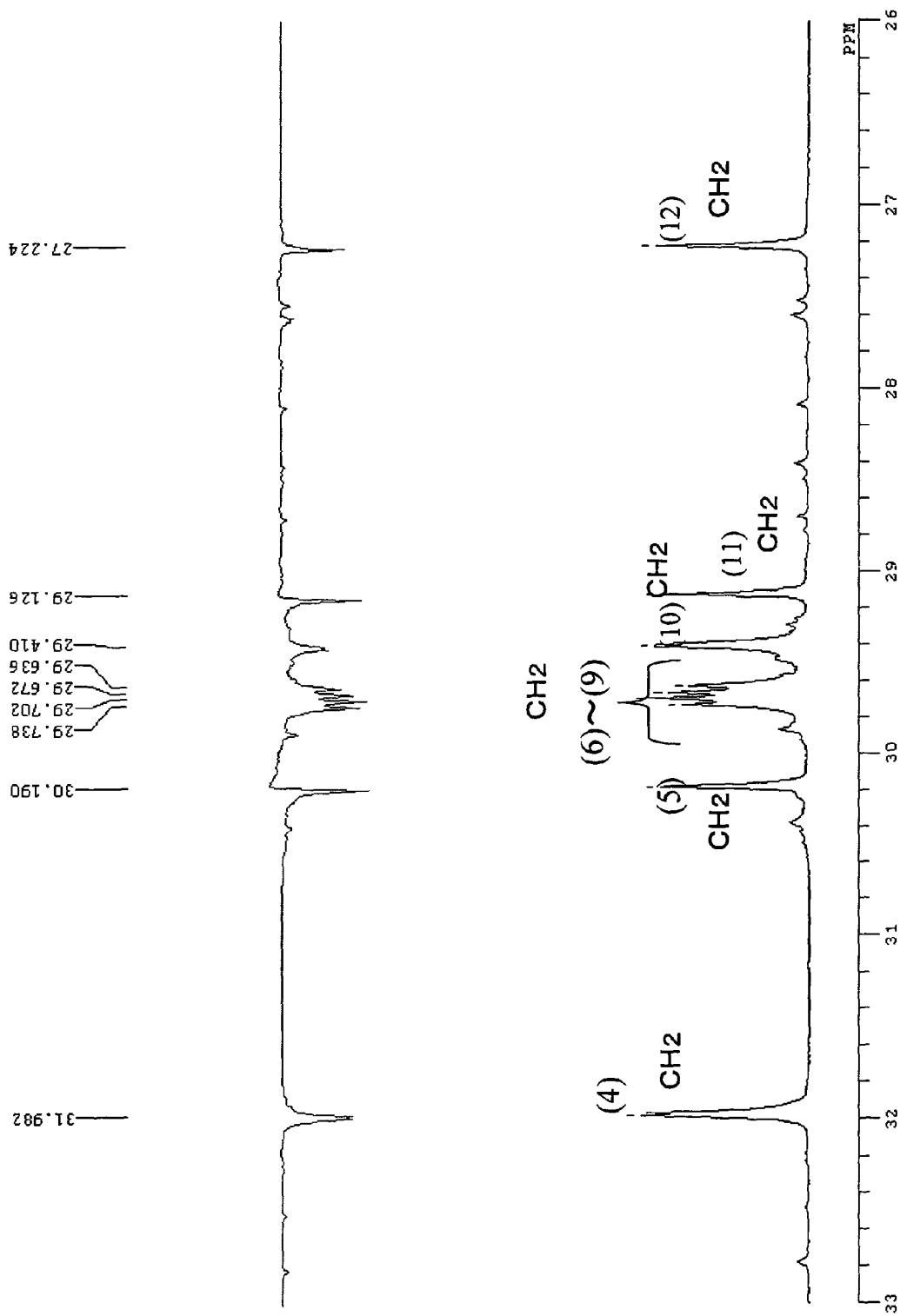
FIG. 5 shows a diagram exhibiting the data profile of $^{13}$C-NMR in the detailed analysis of a 1,3-dioxolane compound.

The results of the detailed analysis of the 1,3-dioxolane compound are shown in FIGS. 3, 4 and 5. FIG. 3 shows a diagram exhibiting the data profile of $^1$H-NMR. Chemical shifts of hydrogen atoms are shown in the diagram. FIGS. 4 and 5 show diagrams exhibiting the data profiles of $^{13}$C-NMR. Chemical shifts of carbon atoms are shown in the diagrams. In the diagram exhibiting the data profile of $^1$H-NMR (FIG. 3), the values of coupling of each proton (hydrogen atom) are also shown.

The bonding structures of the hydrogen atoms and the carbon atoms in the 2-(long chain branched alkyl)-1,3-dioxolane compound synthesized above in (3) were analyzed successively based on the diagrams shown in FIGS. 6 to 12. It was found that the compound synthesized above in (3) had the 1,3-dioxolane structure shown in FIGS. 1 and 2.

Figure 6:
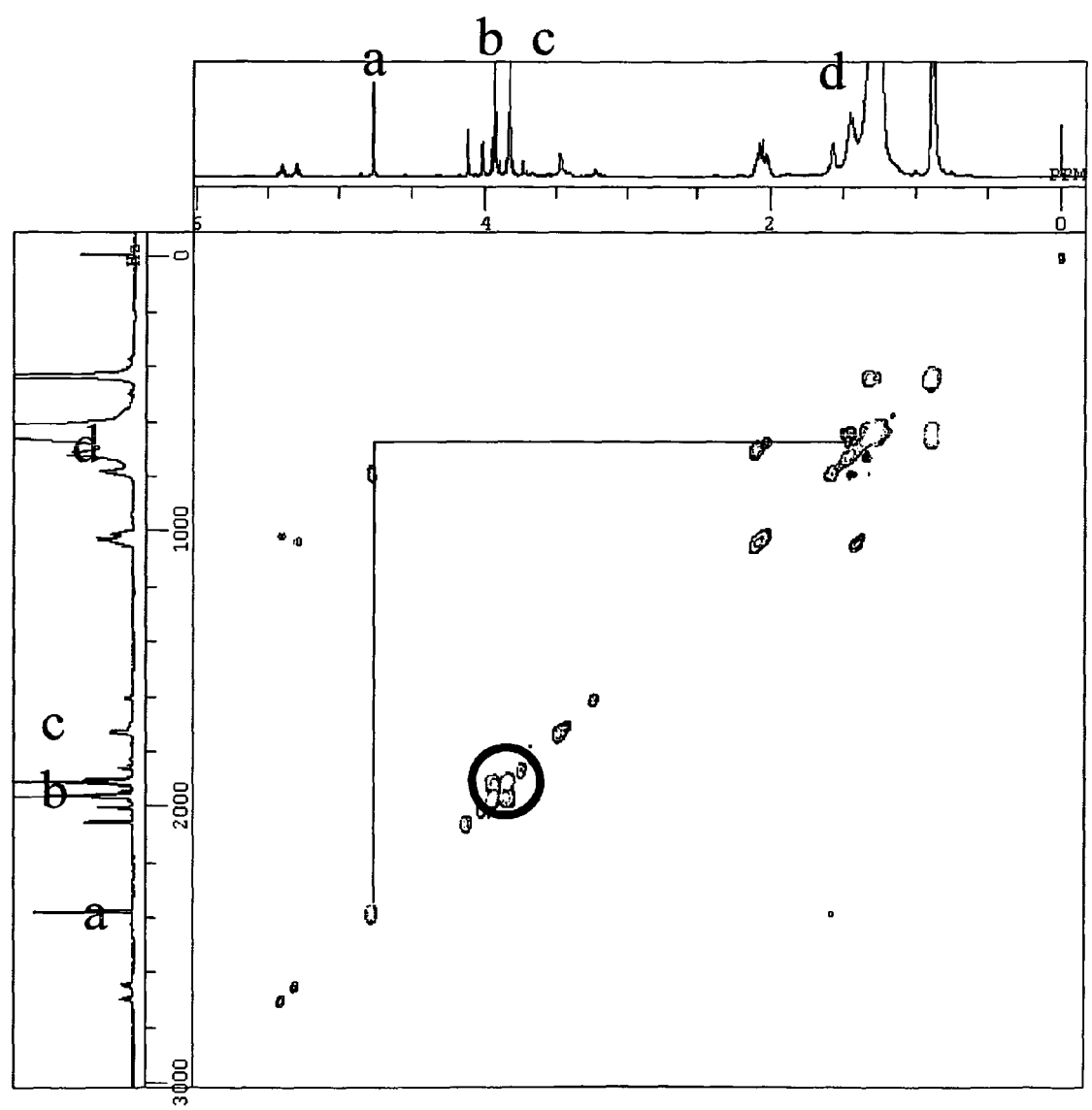
FIG. 6 shows a diagram exhibiting the result of the analysis of a 1,3-dioxolane compound in accordance with the 2D-COSY method.

FIG. 6 shows a diagram exhibiting the result of the analysis in accordance with the 2D-COSY method. It was found from FIG. 6 that a(1H) had the spin bonding with d(1H).

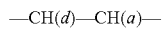

a: 4.77 ppm (d), JH=4.3 Hz d: 1.57 ppm (m), JH=4.3 Hz

It is also found that b(2H) had the spin bonding with c(2H).

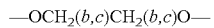

b: 3.94 ppm (m), JH=7.0 Hz c: 3.83 ppm (m), JH=7.0 Hz

Figure 7:
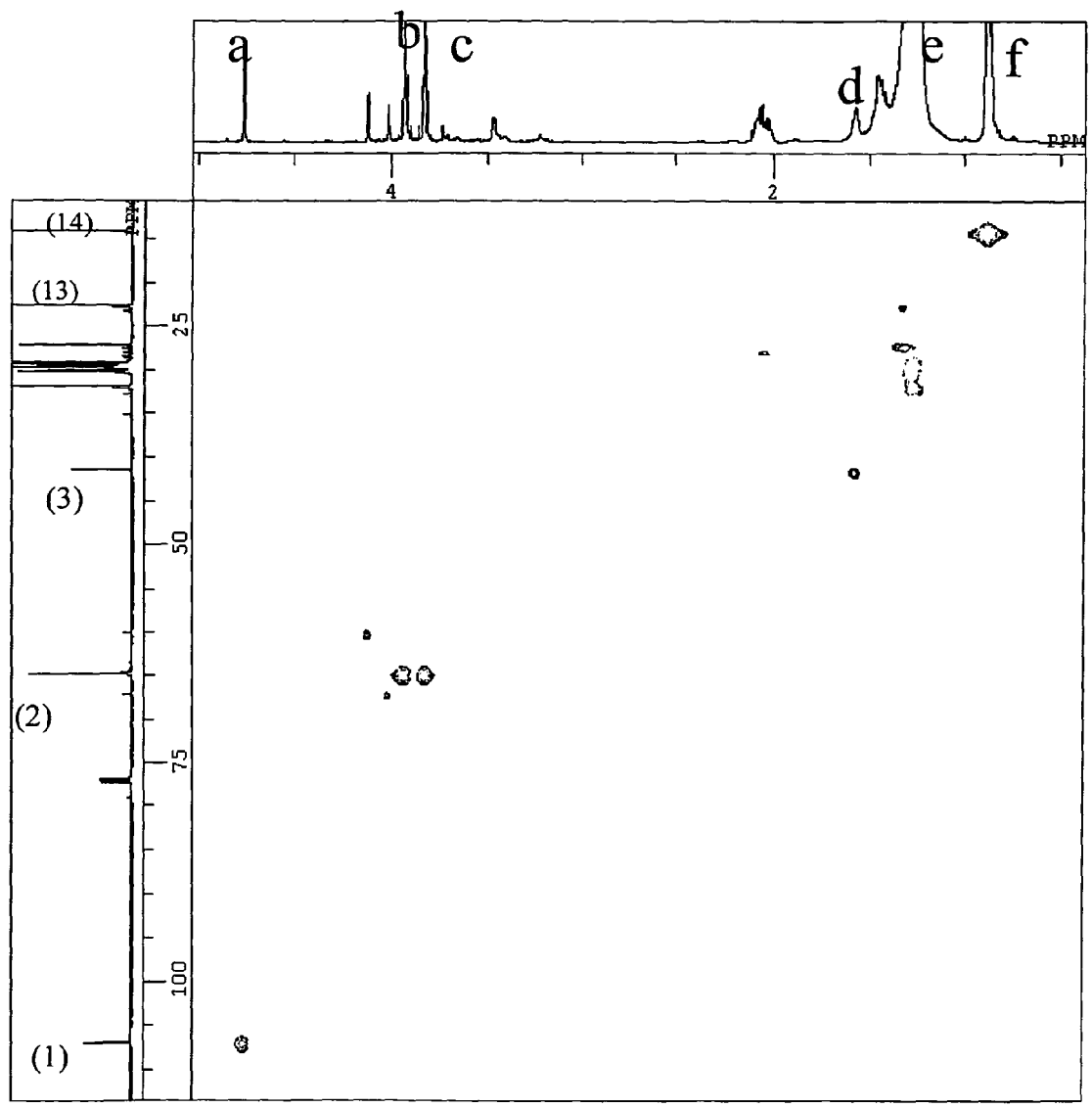
FIG. 7 shows a diagram exhibiting the result of the analysis of a 1,3-dioxolane compound in accordance with the 2D-HMQC method.

FIG. 7 shows a diagram exhibiting the result of the analysis in accordance with the 2D-HMQC method. It is found from FIG. 7 that the CH carbon atom of (1) had the spin bonding with a(1H). It is also found that the $CH_2$ carbon atom of (2) had the spin bonding with b(2H) and c(2H), and the strength of the bond was twice as much as that of (1). It is also found that the CH carbon atom of (3) had the spin bonding with d(1H). These results show the presence of the following unit structures:

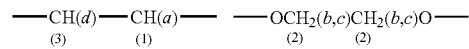

Figure 8:
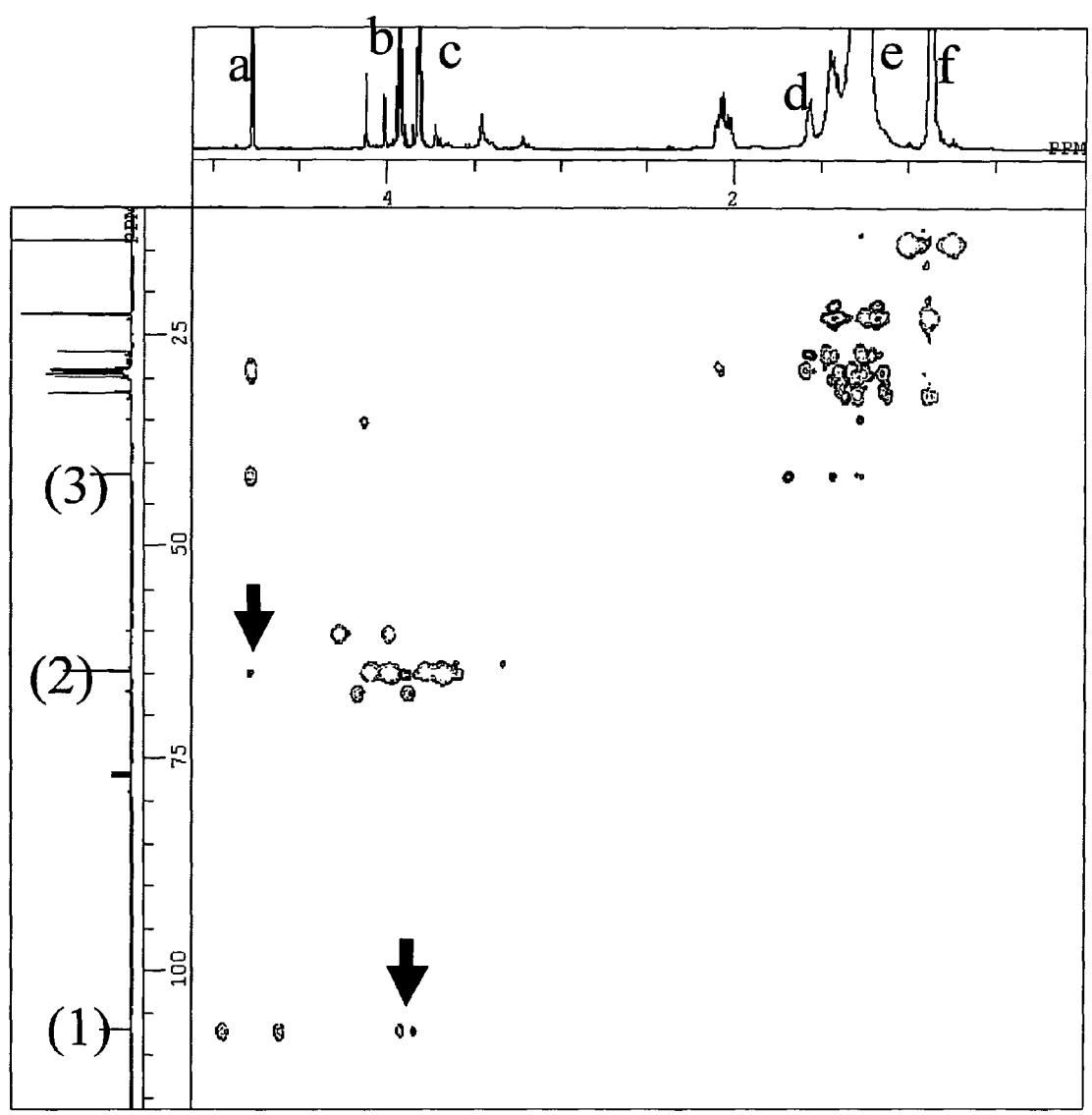
FIG. 8 shows a diagram exhibiting the result of the analysis of a 1,3-dioxolane compound in accordance with the 2D-HMBC method.

FIG. 8 shows a diagram exhibiting the result of the analysis in accordance with the 2D-HMBC method. It was found from FIG. 8 that the CH carbon atom of (1) had the distant spin bonding ($^3J_{CH}$) with the b, c protons, and the $CH_2$ carbon atom of (2) had the distant spin bonding ($^3J_{CH}$) with the a proton ($^3J_{CH}$=3~9 Hz). These results show the presence of the following unit structure:

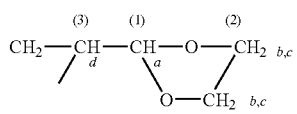

Figure 9:
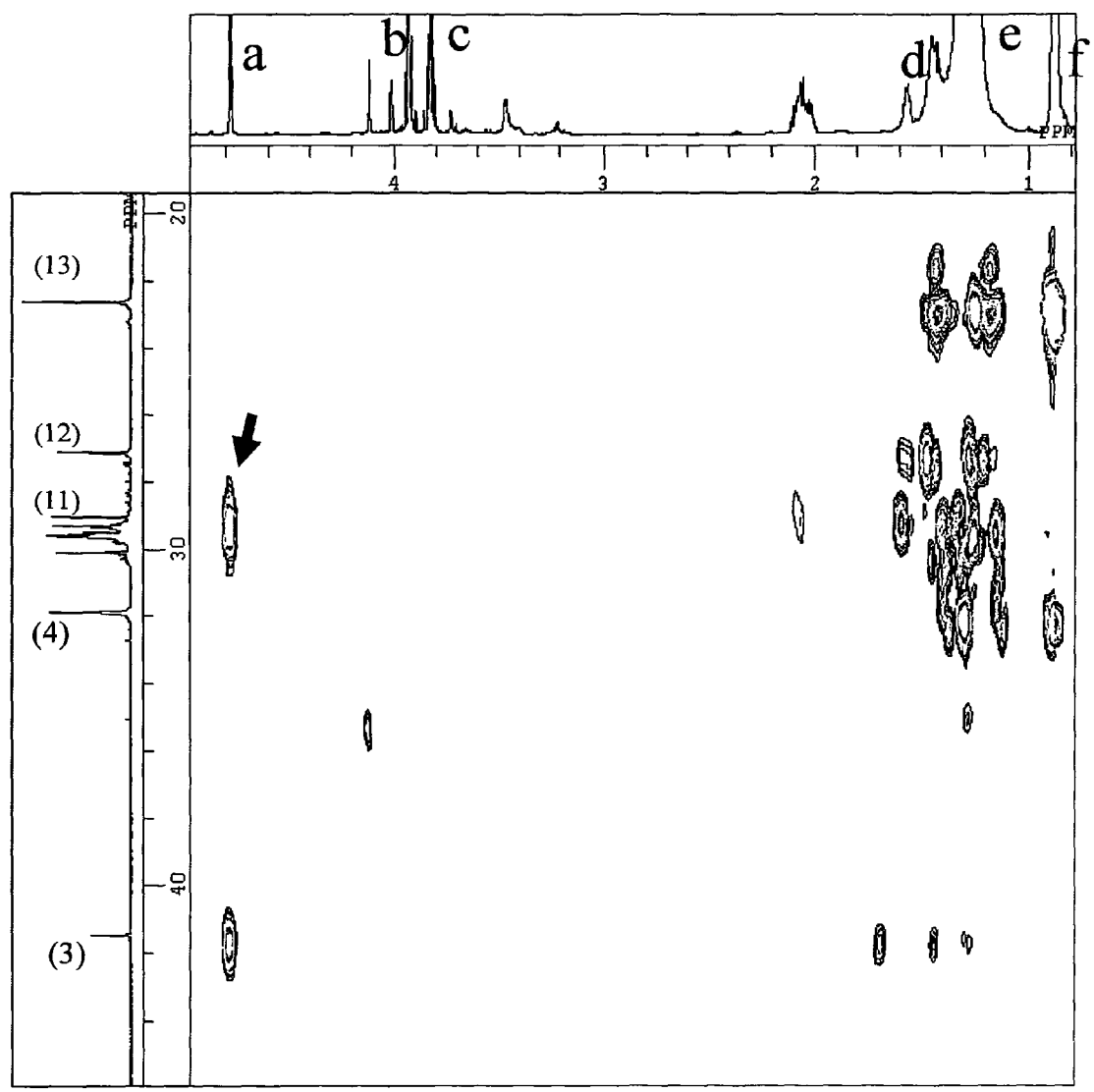
FIG. 9 shows a diagram exhibiting the result of the analysis of a 1,3-dioxolane compound in accordance with the 2D-HMBC method.

FIG. 9 shows a diagram exhibiting the result of the analysis in accordance with the 2D-HMBC method. It was found from FIG. 8 that the $CH_2$ carbon atom of (11) had the distant spin bonding ($^3J_{CH}$) with the a proton. This result shows the presence of the following unit structure:

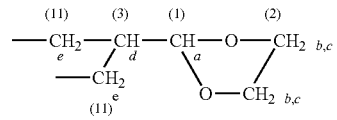

Figure 10:
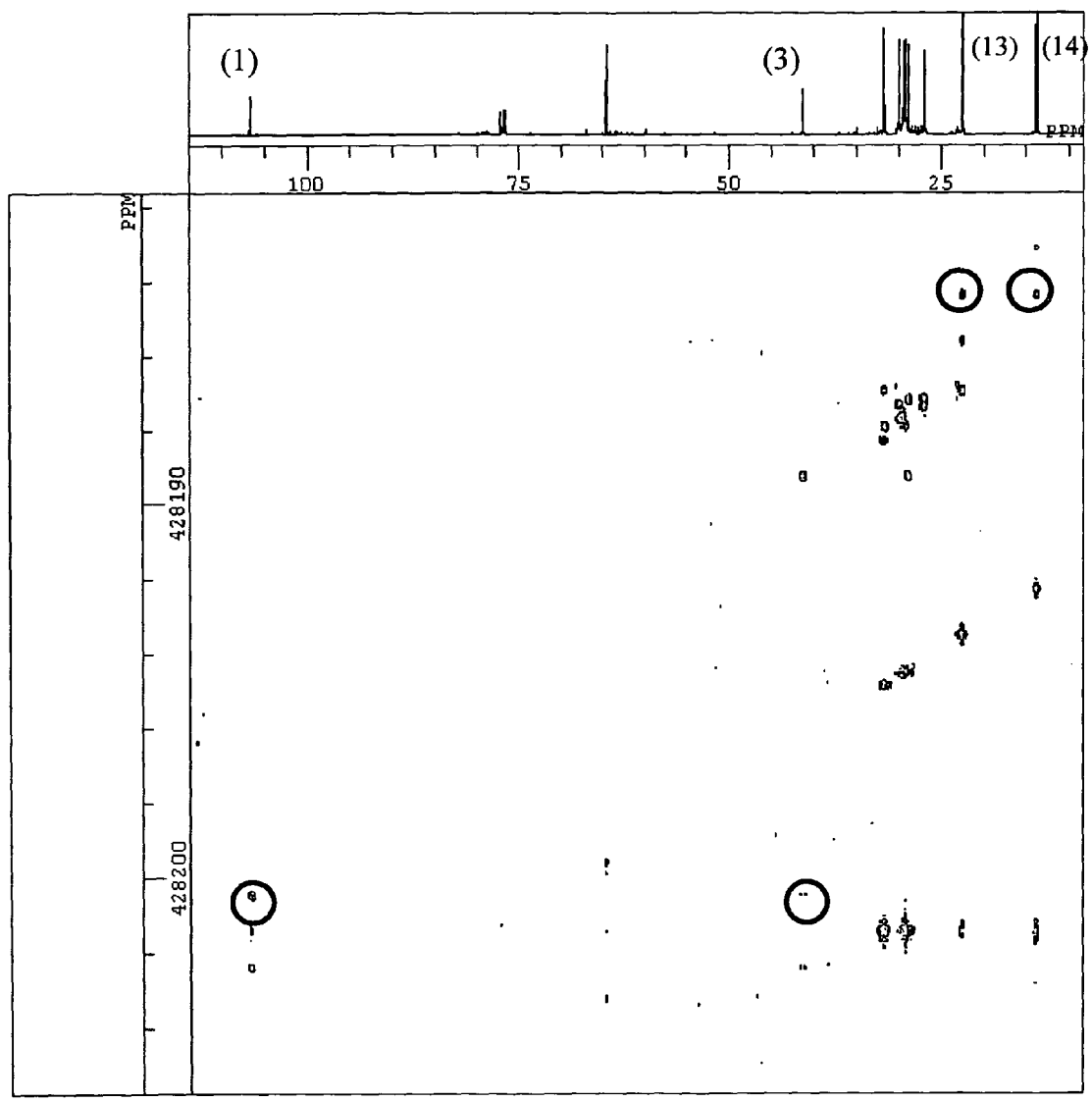
FIG. 10 shows a diagram exhibiting the result of the analysis of a 1,3-dioxolane compound in accordance with the 2D-INADEQUATE method.

FIG. 10 shows a diagram exhibiting the result of the analysis in accordance with the 2D-INADEQUATE method. It was found from FIG. 10 that the CH carbon atom of (1) was bonded with the CH carbon atom of (3), and the $CH_3$ carbon atom of (14) was bonded with the $CH_2$ carbon atom of (13).

Figure 11:
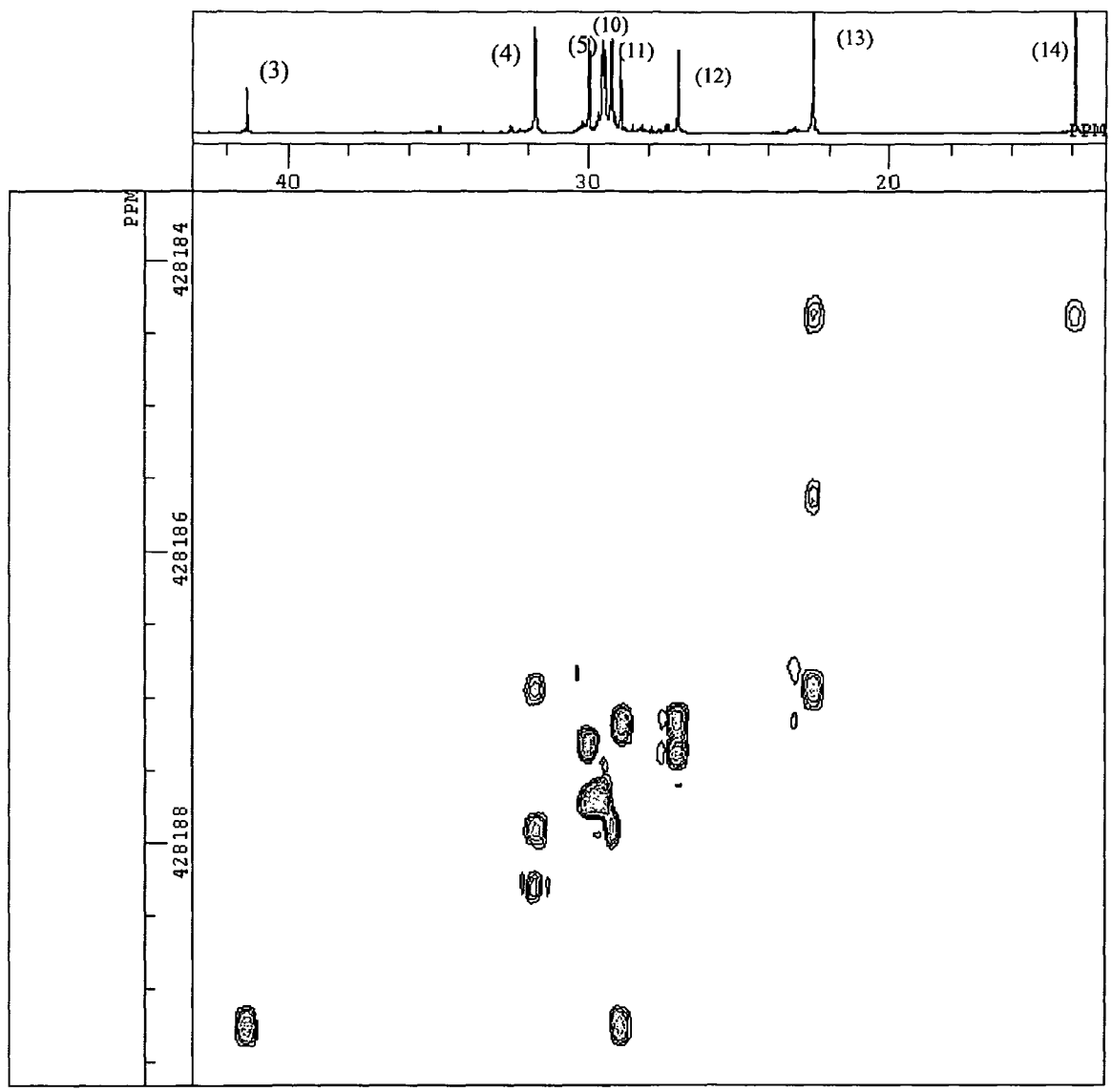
FIG. 11 shows a diagram exhibiting the result of the analysis of a 1,3-dioxolane compound in accordance with the 2D-INADEQUATE method.

FIG. 11 shows a diagram exhibiting the result of the analysis of in accordance with the 2D-INADEQUATE method. It was found from FIG. 11 that the CH carbon atom of (3) was bonded with the $CH_2$ carbon atom of (11), the $CH_2$ carbon atom of (11) was bonded with the $CH_2$ carbon atom of (12), the $CH_2$ carbon atom of (12) was bonded with the $CH_2$ carbon atom of (5), the $CH_3$ carbon atom of (14) was bonded with the $CH_2$ carbon atom of (13), the $CH_2$ carbon atom of (13) was bonded with the $CH_2$ carbon atom of (4), and the $CH_2$ carbon atom of (4) was bonded with the $CH_2$ carbon atom of (10).

Figure 12:
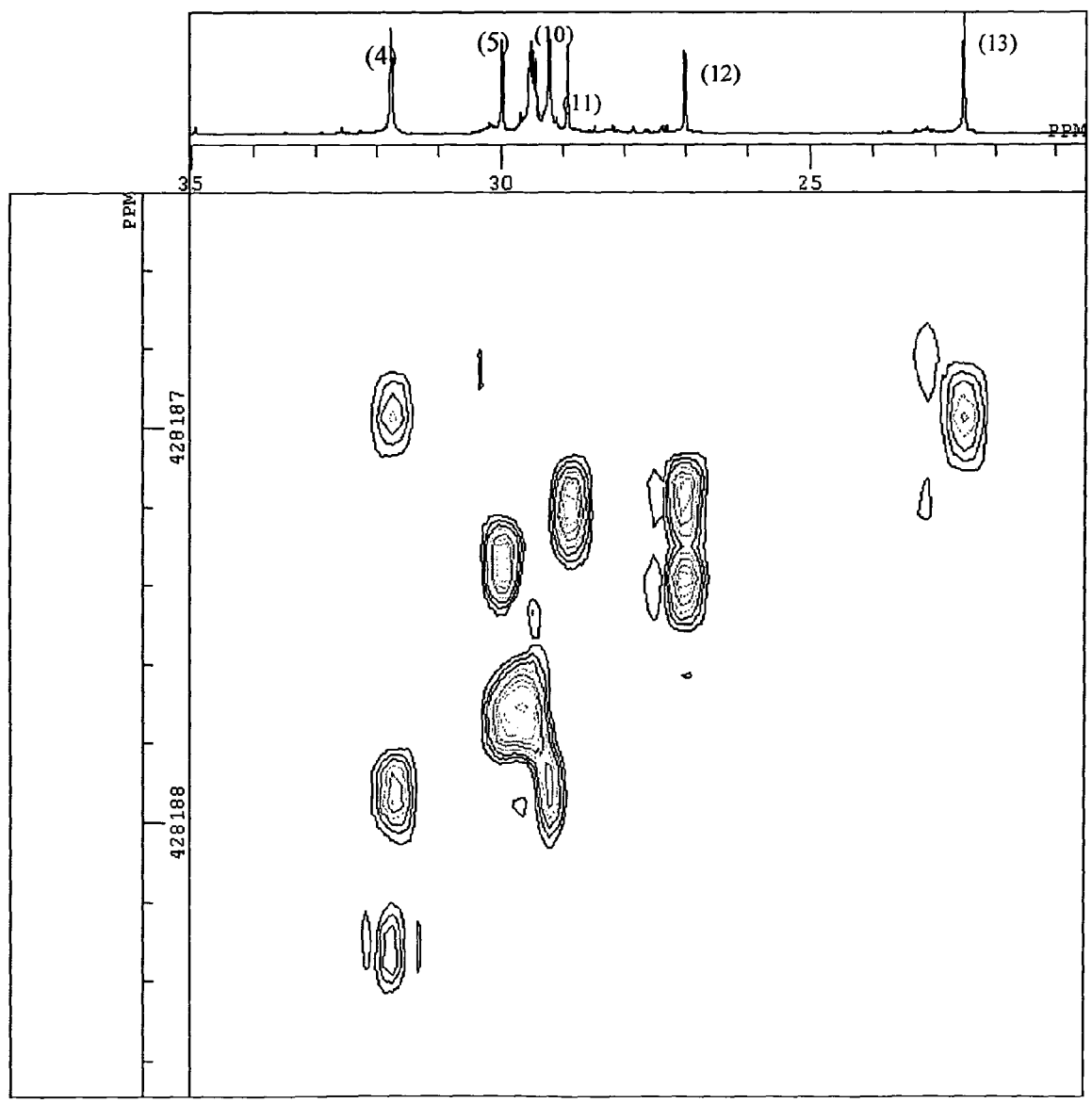
FIG. 12 shows a partially expanded diagram of FIG. 11.

FIG. 12 shows a partially expanded diagram of FIG. 11.

Example 2

Synthesis of a 2-(long chain branched alkyl)-1,3-dioxolane (1) Synthesis of 2-octyl-1-dodecylaldehyde Into a three-necked flask having an inner volume of 1 liter, 200 g (0.67 moles) of 2-octyl-1-dodecanol (manufactured by ALDRICH Corporation; the product number: 46, 448-1) and 23 g of chromium oxide(VI) (manufactured by KANTO KAGAKU Co., Ltd.; the product number: 07355-00) were placed. After the reaction mixture was stirred at the room temperature for 18 hours, the reaction temperature was slowly elevated to 60° C. over 2 hours, and the stirring was continued at this temperature for 4 hours. After the reaction was completed, the formed solid substances were separated by filtration. The reaction product was washed with an aqueous solution of sodium hydrogencarbonate having a concentration of 5% by mass and dried. The reaction product was then distilled under a reduced pressure, and 112 g (the crude yield: 56%) of a fraction of 125 to 135° C. [the pressure: 13.3 Pa (0.1 Torr)] was obtained. This fraction was analyzed in accordance with the gas chromatography, and it was found that the content of 2-octyl-1-dodecylaldehyde was 78%.

(2) Synthesis of a 2-(long chain branched alkyl)-1,3-dioxolane

Into a three-necked flask having an inner volume of 500 ml and equipped with a dropping funnel and a reflux condenser, 200 ml of ethylene glycol (manufactured by WAKO JUN-YAKU Co., Ltd; Special Reagent Grade) and 2 g of concentrated sulfuric acid (the concentration: 96% by mass or greater) were placed, and the content was heated at 60° C. While the content was stirred at this temperature, 42.5 g (0.143 moles) of 2-octyl-1-dodecylaldehyde synthesized above in (1) was slowly added dropwise over 15 hours. After the addition was completed, the resultant mixture was stirred for 5 hours, and then the temperature was lowered. The reaction product was treated by the liquid-liquid separation, and the upper layer was washed with water and dried. A reaction product (a concentrated product) in an amount of 49.5 g was obtained as the result of these operations.

Then, 20.0 g of the reaction product was dissolved into hexane, and the obtained solution was developed in a column packed with 200 g of silica gel (the moving phase: hexane). Then, the development was further conducted with 1 liter of a mixed solvent containing hexane and diethyl ether in relative amounts by volume of 95:5. Thus, 10.2 g (the yield: 49.3% by mole) of a 2-(long chain branched alkyl(the number of carbon atoms: 19))-1,3-dioxolane compound (the same compound as that obtained in Example 1) was obtained.

Application Example 1

Test of the Lubricating Property of the Dioxolane Compound

Using 85 parts by mass of polyisobutylene (the kinematic viscosity at 40° C.: 850 mm$^2$/s) as the base oil of the lubricant, a lubricating oil composition for metalworking was prepared by adding 15 parts by mass of the 2-(long chain branched alkyl)-1,3-dioxolane synthesized in Example 1(3) to the base oil. For comparison, another lubricating oil composition for metalworking was prepared by adding 15 parts by mass of butyl stearate to 85 parts by mass of polyisobutylene used above. The lubricating property of the above lubricating oil compositions was evaluated in accordance with the following methods. The lubricating oil composition prepared by using the 2-(long chain branched alkyl)-1,3-dioxolane had a friction coefficient of 0.13, and the lubricating oil composition prepared by using butyl stearate had a friction coefficient of 0.28. This result shows that the lubricating oil composition prepared by using the 2-(long chain branched alkyl)-1,3-dioxolane had the remarkably improved friction coefficient and could be advantageously used as the lubricating oil composition for metalworking.

| [Condition of the friction test by reciprocal movements] | |
| --- | --- |
| Tester: | A reciprocally sliding friction tester |
| Test load: | 4.9 N |
| Sliding speed: | 20 mm/s |
| Test temperature: | 150° C. |
| Sliding distance: | 50 mm |
| Number of the reciprocal movement: | 50 |
| Test piece (plate): | C-1220 |
| Test piece (ball): | SUJ2 |
| Item of evaluation: | friction coefficient after 50 reciprocal movements |

Example 3

Synthesis of 2-(1-butylheptyl)-1,3-dioxolane

In accordance with similar procedures to those conducted in Example 1(1) except that 1-hexene was used in place of 1-decene used in Example 1(1), a dimer of hexene was synthesized, and 2-butyl-1,2-epoxyoctane was synthesized using the obtained dimer of hexene in accordance with procedures similar to those conducted in Example 1(2). In accordance with similar procedures to those conducted in Example 1(3) except that 2-butyl-1,2-epoxyoctane was used in place of 2-octyl-1,2-epoxydodecane used in Example 1(3), 2-(1-butylheptyl)-1,3-dioxolane was obtained.

Example 4

Synthesis of 2-(1-hexylnonyl)-1,3-dioxolane

In accordance with similar procedures to those conducted in Example 1(1) except that 1-octene was used in place of 1-decene used in Example 1(1), a dimer of octene was synthesized, and 2-hexyl-1,2-epoxydecane was synthesized using the obtained dimer of octene in accordance with procedures similar to those conducted in Example 1(2). In accordance with similar procedures to those conducted in Example 1(3) except that 2-hexyl-1,2-epoxydecane was used in place of 2-octyl-1,2-epoxydodecane used in Example 1(3), 2-(1-hexylnonyl)-1,3-dioxolane was obtained.

Example 5

Synthesis of 2-(1-octylundecyl)-α,β-glycerol formal

In accordance with similar procedures to those conducted in Example 1(3) except that glycerol was used in place of ethylene glycol used in Example 1(3), 2-(1-octylundecyl)-α,β-glycerol formal was obtained.

Example 6

Synthesis of 2-(1-octenylundecyl)-1,3-dioxolane

In accordance with similar procedures to those conducted in Example 1(3) except that 2-octenyl-1,2-epoxydodecane was used in place of 2-octyl-1,2-epoxydodecane used in Example 1(3), 2-(1-octenylundecyl)-α,β-glycerol formal was obtained.

Examples 7 to 15 and Comparative Examples 1 to 4

Figure 13:
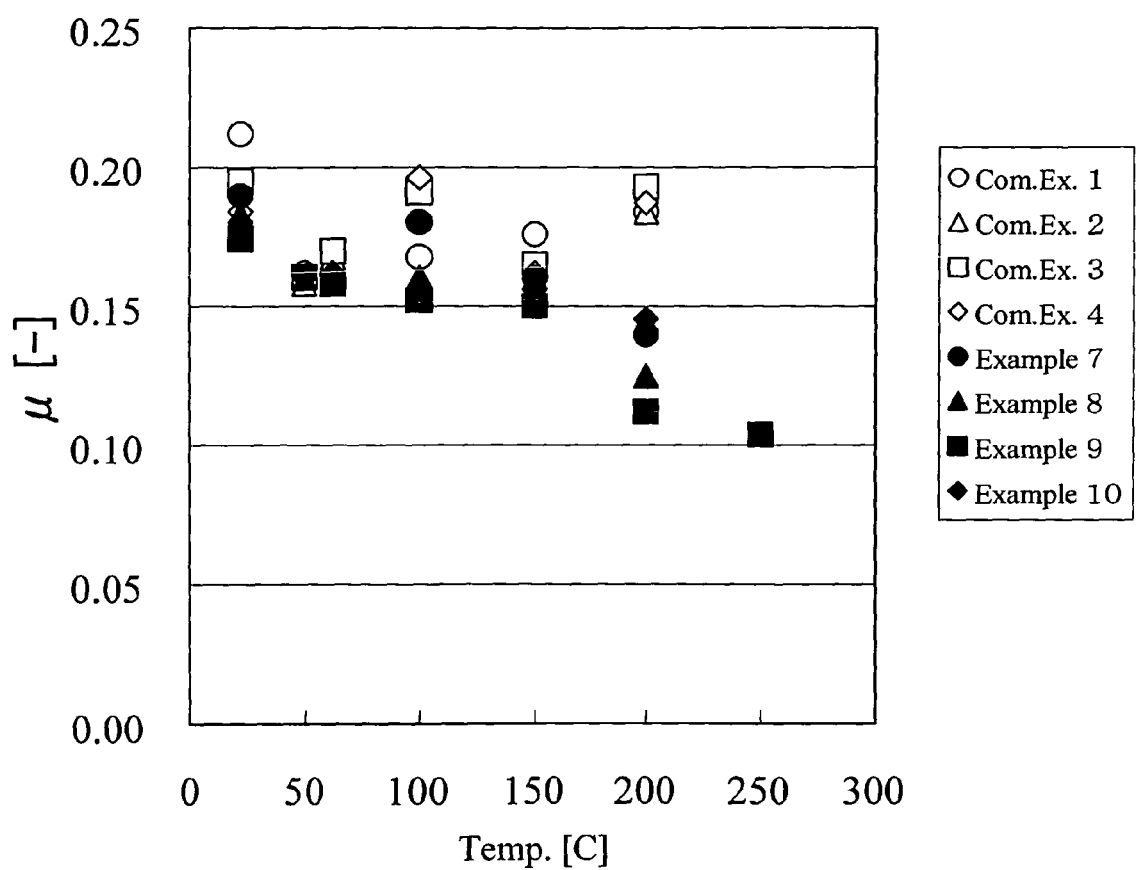
FIG. 13 shows a diagram exhibiting the results of the friction test by reciprocal movements in Examples and Comparative Examples.
Figure 14:
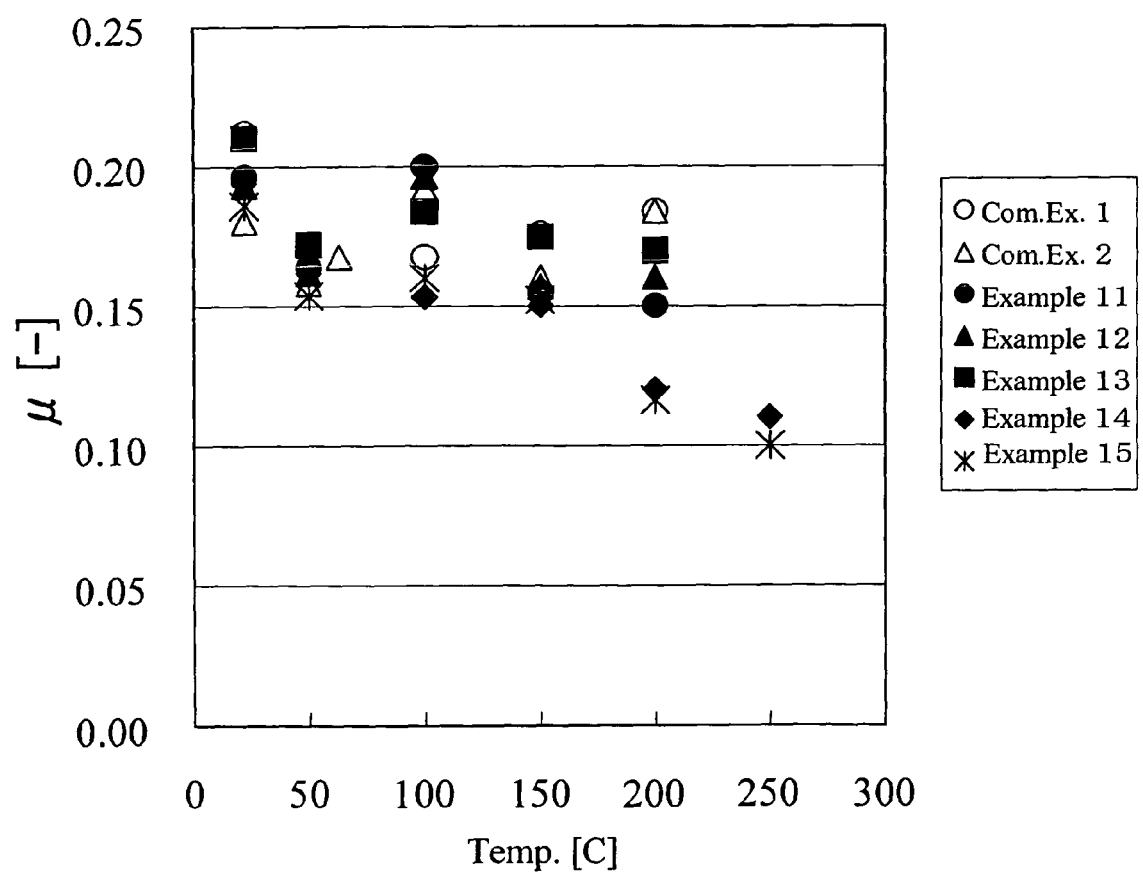
FIG. 14 shows a diagram exhibiting the results of the friction test by reciprocal movements in Examples and Comparative Examples.
Figure 15:
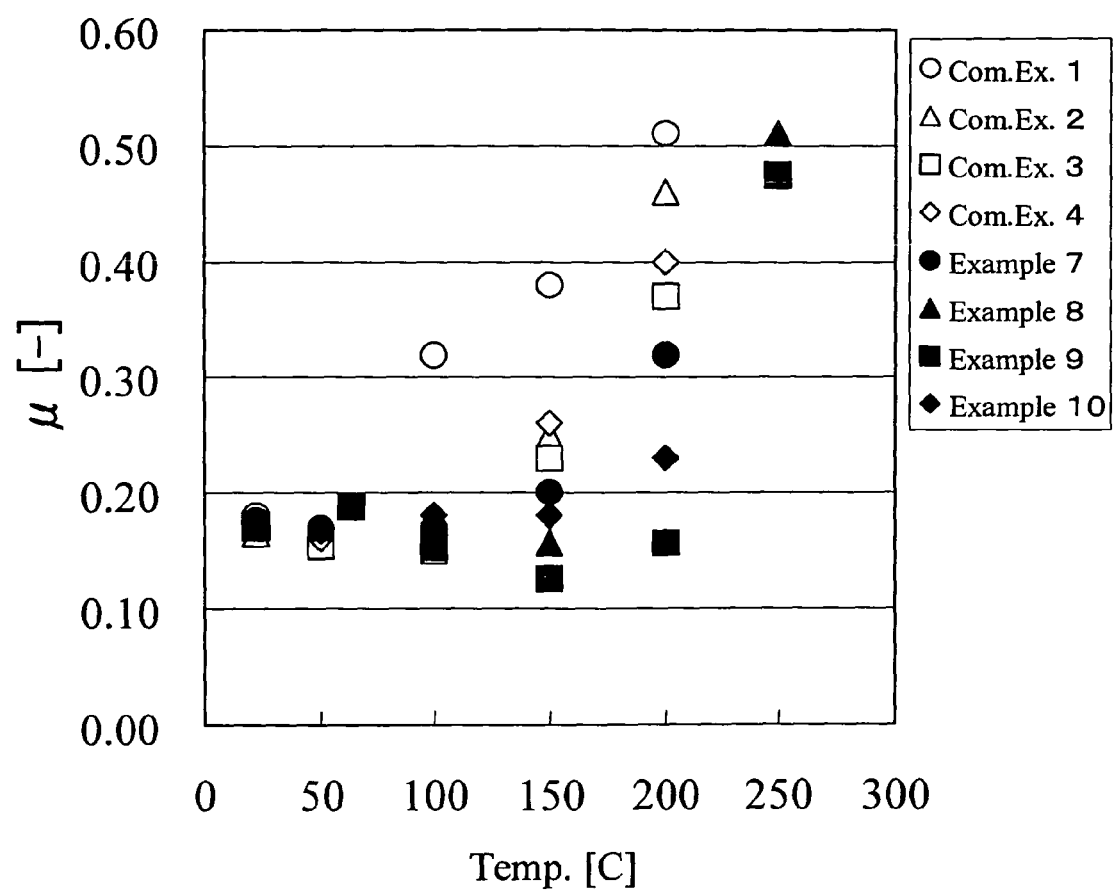
FIG. 15 shows a diagram exhibiting the results of the friction test by reciprocal movements in Examples and Comparative Examples.
Figure 16:
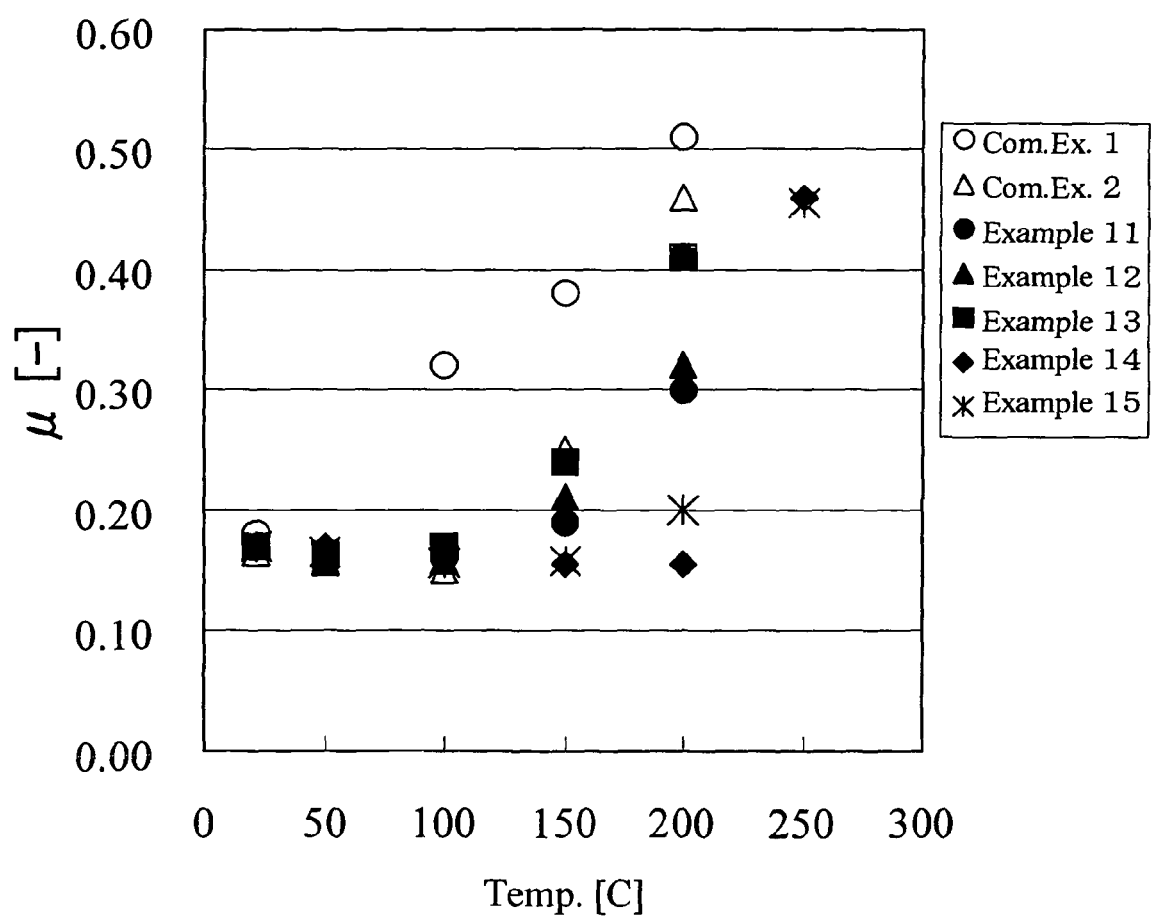
FIG. 16 shows a diagram exhibiting the results of the friction test by reciprocal movements in Examples and Comparative Examples.

Components of the types shown in Table 1 in the amounts also shown in Table 1 were mixed together, and lubricating oil compositions were prepared. Using the obtained lubricating oil compositions, the friction test by reciprocal movements and the test of flat plate drawing were conducted, and the lubricating property was evaluated. The results of the friction test by reciprocal movements are shown in FIGS. 13 to 16, and the results of the test of flat plate drawing are shown in Table 1. FIGS. 13 and 14 shows the change in the average friction coefficient in the first to the fifth reciprocal movements with temperature. FIGS. 15 and 16 shows the change in the average friction coefficient in the 45th to the 50th reciprocal movements with temperature.

For the evaluation of the annealing property, test plates made of pure copper were used. In Annealing test 1 in which a test plate having a depression was used, the change in the color of the plate and the presence or the absence of residues were examined after the test had been completed. In Annealing test 2 in which a flat plate was used, the amount of the residual oil was measured.

| [Condition of the friction test by reciprocal movements] | |
| --- | --- |
| Tester: | A reciprocally sliding friction tester |
| Test load: | 4.9 N |
| Sliding speed: | 20 mm/s |

-continued

[Condition of the friction test by reciprocal movements]

| | |
|---|---|
| Test temperature: | 30 to 250° C. |
| Sliding distance: | 50 mm |
| Number of the reciprocal movement: | 50 |
| Test piece (plate): | C-1220 |
| Test piece (ball): | SUJ2 |
| Item of evaluation: | average friction coefficient in the first to the fifth reciprocal movements and average friction coefficient in the 45th to the 50th reciprocal movements |

[Condition of the test of flat plate drawing]

| | |
|---|---|
| Tester: | INSTRON tester |
| Decrease in area: | 33% |
| Sliding speed: | 200 mm/s |
| Test temperature: | 22° C. |
| Sliding distance: | 150 mm |
| Test piece (plate): | C-1220 (25 mm × 300 mm × 1 mm) |
| Punch: | WC (2R) |
| Item of evaluation: | comparison of the average resistance of drawing |

[Annealing Test 1]

1. A lubricating oil composition in an amount of 10 mg was placed into a depression (the diameter: 7 mm; the depth: 5 mm) of a test plate made of pure copper, and the depression was tightly sealed with a cap of a copper plate using bolts.

2. The obtained test piece was placed in a heated furnace, and the inside of the furnace was purged with nitrogen.

3. After the purging with nitrogen, the temperature was elevated to 550° C. in 20 minutes, kept at 550° C. for 20 minutes and then lowered under the atmosphere of nitrogen. The test pieces was taken out.

4. The formation of sludge is examined using a camera, and the condition was evaluated by visual observation.

[Annealing Test 2]

1. Both faces of a test plate made of pure copper (60 mm×80 mm) were coated with a lubricating oil composition. Five test plates coated with the composition in this manner were laid on top of another and held together tightly with bolts and nuts at four positions.

2. The composition in an excessive amount was removed at the room temperature in 2 hours, and the combined test plates were annealed in a muffle furnace heated at 500° C. for 20 minutes under a nitrogen stream.

3. After the test plates were cooled, the mass of three test plates at the inside among the five test plates was measured, and the amount of the residual oil per unit area was calculated.

4. The obtained value was converted into the value per unit length assuming that the diameter of a copper tube was 6.35 mm.

TABLE 1

| Component of composition (% by mass) | Kinematic viscosity at 40° C. (mm²/s) | Comparative Example 1 | 2 | 3 | 4 | Example 7 | 8 | 9 |
|---|---|---|---|---|---|---|---|---|
| Polybutene*1 | 1500 | 99.9 | 84.9 | 94.9 | | 84.9 | 84.9 | 84.9 |
| Polyisobutylene*2 | 1500 | | | | 84.9 | | | |
| Polyalkylene glycol insoluble in water*3 | 1500 | | | | | | | |
| Butyl stearate*4 | | | 15.0 | | 15.0 | | | |
| 2-Ethylhexyl stearate*5 | | | | 15.0 | | | | |
| 2-(1-Butylheptyl)-1,3-dioxolane*6 | | | | | | 15.0 | | |
| 2-(1-Hexylnonyl)-1,3-dioxolane*7 | | | | | | | 15.0 | |
| 2-(1-Octylundecyl)-1,3-dioxolane*8 | | | | | | | | 15.0 |
| 2-(1-Octylundecyl)-α,β-glycerol formal*9 | | | | | | | | |
| 2-(1-Octenylundecyl)-1,3-dioxolane*10 | | | | | | | | |
| 2-Octyl-1,2-epoxydodecane*11 | | | | | | | | |
| Benzotriazole*12 | | 0.1 | 0.1 | 0.1 | 0.1 | 0.1 | 0.1 | 0.1 |
| Load of drawing plate (N) | | 4341 | 3625 | 3606 | 3783 | 3283 | 3244 | 3136 |
| Annealing test 1 — residues | | little | none | little | none | none | none | none |
| change in color | | none | none | little | none | none | none | none |
| attachment of cap | | none | found | found | found | none | none | none |
| Annealing test 2 — amount of residual oil (mg/m) | | 0.31 | 0.10 | 0.11 | 0.18 | 0.06 | 0.07 | 0.08 |

| Component of composition (% by mass) | Kinematic viscosity at 40° C. (mm²/s) | Example 10 | 11 | 12 | 13 | 14 | 15 |
|---|---|---|---|---|---|---|---|
| Polybutene*1 | 1500 | 84.9 | 84.9 | | 84.9 | 83.9 | |
| Polyisobutylene*2 | 1500 | | | 84.9 | | | |
| Polyalkylene glycol insoluble in water*3 | 1500 | | | | | | 84.9 |
| Butyl stearate*4 | | | | | | | |
| 2-Ethylhexyl stearate*5 | | | | | | | |
| 2-(1-Butylheptyl)-1,3-dioxolane*6 | | | | | | | |
| 2-(1-Hexylnonyl)-1,3-dioxolane*7 | | | | | | | |
| 2-(1-Octylundecyl)-1,3-dioxolane*8 | | | | 15.0 | | 15.0 | 15.0 |

TABLE 1-continued

| | | | | | | | |
|---|---|---|---|---|---|---|---|
| 2-(1-Octylundecyl)-α,β-glycerol formal*9 | | 15.0 | | | | | |
| 2-(1-Octenylundecyl)-1,3-dioxolane*10 | | | | 15.0 | 15.0 | | |
| 2-Octyl-1,2-epoxydodecane*11 | | | | | | 1.0 | |
| Benzotriazole*12 | | 0.1 | 0.1 | 0.1 | 0.1 | 0.1 | 0.1 |
| Load of drawing plate (N) | | 3214 | 3391 | 3440 | 3508 | 3156 | 3185 |
| Annealing test 1 | residues | none | none | none | none | none | none |
| | change in color | none | none | none | none | none | none |
| | attachment of cap | none | none | none | none | none | none |
| Annealing test 2 | amount of residual oil (mg/m) | 0.09 | 0.09 | 0.09 | 0.09 | 0.10 | 0.09 |

Notes:
*1Manufactured by IDEMITSU KOSAN Co., Ltd.; the trade name: 100R
*2Manufactured by EXXON CHEMICAL Company
*3Polyoxybutylene glycol mono-n-butyl ether
*4Manufactured by KAO Co., Ltd.
*5A commercial product
*6The compound of Preparation Example 2
*7The compound of Preparation Example 3
*8The compound of Preparation Example 1
*9The compound of Preparation Example 4
*10The compound of Preparation Example 5
*11The compound of Preparation Example 1(2)
*12Manufactured by JOHOKU KAGAKU Co., Ltd.; the trade name: BT-120

Example 16 and Comparative Example 5

Components of the types shown in Table 2 in the amounts also shown in Table 2 were mixed together, and lubricating oil compositions were prepared. Using the obtained lubricating oil compositions, drawing was conducted under the following condition, and the defect fraction in squeezing and wear of the tool were evaluated. The results are shown in Table 2.

| [Condition of drawing] | |
|---|---|
| Pressing machine: | 150 ton press (manufactured by Burrak Company) |
| Material of plate: | C1220 |
| Material of tool: | high-speed steel |
| Stroke speed: | 0.5 m/sec |
| Degree of squeezing: | 55% |
| Shape of formed hole: | 6.35/20.32 mm (2.5/8 inch) (circular) |
| Working time: | 300 cycles/min. × 5 minutes |

TABLE 2

| Component of composition (% by mass) | Example 16 | Comparative Example 5 |
|---|---|---|
| Polybutene (kinematic viscosity at 40° C.: 130 mm$^2$/m)*1 | 84.9 | 84.9 |
| Butyl stearate*2 | | 15.0 |
| 2-(1-Octylundecyl)-1,3-dioxolane*3 | 15.0 | |
| Benzotriazole*4 | 0.1 | 0.1 |
| Defect fraction in squeezing (%) | 4 | 18 |
| Wear of tool | none | little |

Notes:
*1Manufactured by IDEMITSU KOSAN Co., Ltd.; the trade name: 5H
*2Manufactured by KAO Co., Ltd.
*3The compound of Example 1
*4Manufactured by JOHOKU KAGAKU Co., Ltd.; the trade name: BT-120

Comparative Example 6 and Examples 17 and 18

Components of the types shown in Table 3 in the amounts also shown in Table 3 were mixed together, and lubricating oil compositions were prepared. Using the obtained lubricating oil compositions, the rolling experiment was conducted under the following condition, and the critical draft of rolling due to damages on the surface (heat scratch) was obtained and evaluated. The results are shown in Table 3.

| [Condition of rolling] | |
|---|---|
| Rolling machine: | a four-stage rolling machine |
| Diameter of backup roll: | 200 mm |
| Diameter of work roll: | 40 mm |
| Rolling speed: | 100 m/min. |
| Tension: | 3920 N at the input side, 2156 N at the output side |
| Material for rolling: | C2680 1.0 × 50 mm coil |
| Number of path: | 1 path |
| Draft: | 30 to 65% |

TABLE 3

| Component of composition (% by mass) | Comparative Example 6 | Example 17 | Example 18 |
|---|---|---|---|
| Mineral oil (kinematic viscosity at 40° C.: 8 mm$^2$/m)*1 | 90.0 | 90.0 | 89.0 |
| Butyl stearate*2 | 10.0 | | |
| 2-(1-Octylundecyl)-1,3-dioxolane*3 | | 10.0 | 10.0 |
| 2-Octyl-1,2-epoxydodecane*4 | | | 1.0 |
| Critical draft (%) | 55.0 | >65 | >65 |
| Observation | | no damages on the surface even at 65% | |

Notes:
*1A paraffinic mineral oil
*2Manufactured by KAO Co., Ltd.
*3The compound of Example 1
*4The compound of Example 1(2)

It is apparent from the results shown above that the annealing property and the friction property of the lubricating oil compositions of Examples were remarkably improved.

INDUSTRIAL APPLICABILITY

The alkylacetal compound of the present invention can provide the lubricating oil composition which is advantageously used as the drawing oil composition for producing copper tubes when the alkylacetal compound is mixed with a base oil.

The lubricating oil composition for metalworking of the present invention exhibits the excellent lubricating property (the small friction) at high temperatures and is advantageously used for working of copper-based metals (copper and copper alloy).

The invention claimed is:

1. An alkylacetal compound having a structure represented by formula (3):

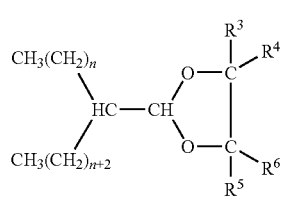

(3)

wherein $R^3$ to $R^6$ each independently represent a hydrogen atom or a hydrocarbon group, and n represents an integer in a range of 7 to 15.

2. A process for producing an alkylacetal compound having a structure represented by formula (2):

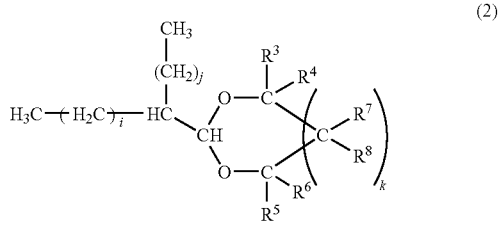

(2)

wherein $R^3$ to $R^8$ each independently represent hydrogen atom or a hydrocarbon group, k represents 0 or 1, and i and j each represent an integer satisfying a relation that a sum of the integers is in a range of 10 to 70, said process comprising reacting an alcohol with an epoxide represented by formula (4):

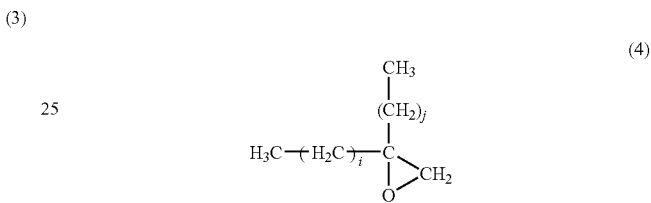

(4)

wherein i and j each represent an integer satisfying a relation that a sum of the integers is in a range of 10 to 70.

* * * * *